United States Patent
Bandaru et al.

(10) Patent No.: US 9,506,060 B2
(45) Date of Patent: Nov. 29, 2016

(54) LNA ANTISENSE OLIGONUCLEOTIDES FOR THE MODULATION OF MYC EXPRESSION

(71) Applicants: Dana-Farber Cancer Institute, Inc., Boston, MA (US); Belrose Pharma Inc., Princeton, NJ (US)

(72) Inventors: Rajanikanth Bandaru, Warren, NJ (US); Yixian Zhang, Piscataway, NJ (US); Zhengxing Qu, Warren, NJ (US); Lee Greenberger, Montclair, NJ (US); Christopher Ott, Boston, MA (US); James Elliott Bradner, Boston, MA (US)

(73) Assignees: DANA-FARBER CANCER INSTITUTE, INC., Boston, MA (US); ENZON PHARMACEUTICALS, INC., Cranford, NJ (US)

( * ) Notice: Subject to any disclaimer, the term of this patent is extended or adjusted under 35 U.S.C. 154(b) by 0 days.

(21) Appl. No.: 14/378,698

(22) PCT Filed: Feb. 15, 2013

(86) PCT No.: PCT/US2013/026515
§ 371 (c)(1),
(2) Date: Aug. 14, 2014

(87) PCT Pub. No.: WO2013/123451
PCT Pub. Date: Aug. 22, 2013

(65) Prior Publication Data
US 2016/0024495 A1 Jan. 28, 2016

Related U.S. Application Data

(60) Provisional application No. 61/598,995, filed on Feb. 15, 2012.

(51) Int. Cl.
*C07H 21/02* (2006.01)
*C07H 21/04* (2006.01)
*A61K 31/70* (2006.01)
*C12N 15/113* (2010.01)
*A61K 31/711* (2006.01)
*C12N 5/00* (2006.01)

(52) U.S. Cl.
CPC ........... *C12N 15/113* (2013.01); *A61K 31/711* (2013.01); *C12N 15/1135* (2013.01); *C12N 2310/11* (2013.01); *C12N 2310/315* (2013.01); *C12N 2310/3231* (2013.01); *C12N 2310/341* (2013.01); *C12N 2310/351* (2013.01); *C12N 2320/30* (2013.01)

(58) Field of Classification Search
None
See application file for complete search history.

(56) References Cited

U.S. PATENT DOCUMENTS

| 2002/0068709 A1 | 6/2002 | Orum et al. |
| 2006/0154888 A1 | 7/2006 | Rosenbohm et al. |
| 2010/0055782 A1 | 3/2010 | Quay et al. |

FOREIGN PATENT DOCUMENTS

WO 2011/048125 A1 4/2011

*Primary Examiner* — Sean McGarry
(74) *Attorney, Agent, or Firm* — Stoel Rives LLP

(57) ABSTRACT

The disclosure relates to oligonucleotide compounds (oligomers) that target Myc mRNA in a cell, leading to reduced expression of Myc. Reduction of Myc expression is beneficial for the treatment of certain disorders, such as hyperproliferative disorders (e.g., cancer). The disclosure provides therapeutic compositions comprising oligomers and methods for modulating the expression of Myc using said oligomers, including methods of treatment.

20 Claims, 14 Drawing Sheets

SEQUENCE LISTING

<160> NUMBER OF SEQ ID NOS: 48

<210> SEQ ID NO 1
<211> LENGTH: 2379
<212> TYPE: DNA
<213> ORGANISM: Homo sapiens

<400> SEQUENCE: 1

| | | | | | |
|---|---|---|---|---|---|
| gaccccgag | ctgtgctgct | cgcggccgcc | accgcgggc | cccggccgtc | cctggctccc | 60 |
| ctcctgcctc | gagaagggca | gggcttctca | gaggcttggc | gggaaaaaga | acggagggag | 120 |
| ggatcgcgct | gagtataaaa | gccggttttc | ggggctttat | ctaactcgct | gtagtaattc | 180 |
| cagcgagagg | cagagggagc | gagcgggcgg | ccggctaggg | tggaagagcc | gggcgagcag | 240 |
| agctgcgctg | cgggcgtcct | gggaagggag | atccggagcg | aatagggggc | ttcgcctctg | 300 |
| gcccagccct | cccgctgatc | ccccagccag | cggtccgcaa | cccttgccgc | atccacgaaa | 360 |
| cttttgcccat | agcagcgggc | gggcactttg | cactggaact | acaacaccc | gagcaaggac | 420 |
| gcgactctcc | cgacgcgggg | aggctattct | gcccatttgg | ggacacttcc | ccgccgctgc | 480 |
| caggacccgc | ttctctgaaa | ggctctcctt | gcagctgctt | agacgctgga | ttttttttcgg | 540 |
| gtagtggaaa | accagcagcc | tcccgcgacg | atgcccctca | acgttagctt | caccaacagg | 600 |
| aactatgacc | tcgactacga | ctcggtgcag | ccgtatttct | actgcgacga | ggaggagaac | 660 |
| ttctaccagc | agcagcagca | gagcgagctg | cagccccgg | cgcccagcga | ggatatctgg | 720 |
| aagaaattcg | agctgctgcc | caccccgccc | ctgtccccta | gccgccgctc | gggctctgc | 780 |
| tcgccctcct | acgttgcggt | cacacccttc | tcccttcggg | gagacaacga | cggcggtggc | 840 |
| gggagcttct | ccacggccga | ccagctggag | atggtgaccg | agctgctggg | aggagacatg | 900 |
| gtgaaccaga | gtttcatctg | cgacccggac | gacgagacct | tcatcaaaaa | catcatcatc | 960 |
| caggactgta | tgtggagcgg | cttctcggcc | gccgccaagc | tcgtctcaga | gaagctggcc | 1020 |
| tcctaccagg | ctgcgcgcaa | agacagcggc | agcccgaacc | ccgccgcgg | ccacagcgtc | 1080 |
| tgctccacct | ccagcttgta | cctgcaggat | ctgagcgccg | ccgcctcaga | gtgcatcgac | 1140 |
| ccctcggtgg | tcttccccta | ccctctcaac | gacagcagct | cgcccaagtc | ctgcgcctcg | 1200 |
| caagactcca | gcgccttctc | tccgtcctcg | gattctctgc | tctcctcgac | ggagtcctcc | 1260 |
| ccgcagggca | gccccgagcc | cctggtgctc | catgaggaga | caccgcccac | caccagcagc | 1320 |
| gactctgagg | aggaacaaga | agatgaggaa | gaaatcgatg | ttgtttctgt | ggaaaagagg | 1380 |
| caggctcctg | gcaaaaggtc | agagtctgga | tcaccttctg | ctggaggcca | cagcaaacct | 1440 |
| cctcacagcc | cactggtcct | caagaggtgc | cacgtctcca | cacatcagca | caactacgca | 1500 |
| gcgcctcct | ccactcggaa | ggactatcct | gctgccaaga | gggtcaagtt | ggacagtgtc | 1560 |
| agagtcctga | gacagatcag | caacaaccga | aaatgcacca | gcccaggtc | ctcggacacc | 1620 |
| gaggagaatg | tcaagaggcg | aacacacaac | gtcttggagc | gccagaggag | gaacgagcta | 1680 |
| aaacggagct | ttttgccct | gcgtgaccag | atcccggagt | tggaaaacaa | tgaaaaggcc | 1740 |
| cccaaggtag | ttatccttaa | aaaagccaca | gcatacatcc | tgtccgtcca | agcagaggag | 1800 |
| caaaagctca | tttctgaaga | ggacttgttg | cggaaacgac | gagaacagtt | gaaacacaaa | 1860 |
| cttgaacagc | tacggaactc | ttgtgcgtaa | ggaaagtaa | ggaaacgat | tccttctaac | 1920 |
| agaaatgtcc | tgagcaatca | cctatgaact | tgtttcaaat | gcatgatcaa | atgcaacctc | 1980 |
| acaaccttgg | ctgagtcttg | agactgaaag | atttagccat | aatgtaaact | gcctcaaatt | 2040 |
| ggactttggg | cataaaagaa | cttttttatg | cttaccatct | ttttttttc | tttaacagat | 2100 |

| ttgtatttaa gaattgtttt taaaaaattt taagatttac acaatgtttc tctgtaaata | 2160 |
| ttgccattaa atgtaaataa ctttaataaa acgtttatag cagttacaca gaatttcaat | 2220 |
| cctagtatat agtacctagt attataggta ctataaaccc taattttttt tatttaagta | 2280 |
| cattttgctt tttaaagttg attttttct attgttttta gaaaaaataa aataactggc | 2340 |
| aaatatatca ttgagccaaa tcttaaaaaa aaaaaaaa | 2379 |

```
<210> SEQ ID NO 2
<211> LENGTH: 2613
<212> TYPE: DNA
<213> ORGANISM: Homo sapiens

<400> SEQUENCE: 2
```

| gtcatctgtc tggacgcgct gggtggatgc gggggctcc tgggaactgt gttggagccg | 60 |
| agcaagcgct agccaggcgc aagcgcgcac agactgtagc catccgagga caccccgcc | 120 |
| cccccggccc acccggagac acccgcgcag aatcgcctcc ggatcccctg cagtcggcgg | 180 |
| gagtgttgga ggtcggcgcc ggccccgcc ttccgcgccc ccacgggaa ggaagcaccc | 240 |
| ccggtattaa aacgaacggg gcggaaagaa gccctcagtc gccggccggg aggcgagccg | 300 |
| atgccgagct gctccacgtc caccatgccg gcatgatct gcaagaaccc agacctcgag | 360 |
| tttgactcgc tacagccctg cttctacccg gacgaagatg acttctactt cggcggcccc | 420 |
| gactcgaccc cccggggga ggacatctgg aagaagtttg agctgctgcc cacgccccg | 480 |
| ctgtcgccca gccgtggctt cgcggagcac agctccgagc cccgagctg gtcacggag | 540 |
| atgctgcttg agaacgagct gtggggcagc ccggccgagg aggacgcgtt cggcctgggg | 600 |
| ggactgggtg gcctcacccc caacccggtc atcctccagg actgcatgtg gagcggcttc | 660 |
| tccgcccgcg agaagctgga gcgcgccgtg agcgagaagc tgcagcacgg ccgcgggccg | 720 |
| ccaaccgccg gttccaccgc ccagtccccg ggagccggcg ccgccagccc tgcgggtcgc | 780 |
| gggcacggcg gggctgcggg agccggccgc gccggggccg ccctgccccgc cgagctcgcc | 840 |
| cacccggccg ccgagtgcgt ggatcccgcc gtggtcttcc cctttcccgt gaacaagcgc | 900 |
| gagccagcgc ccgtgcccgc agccccggcc agtgccccgg cggcgggccc tgcggtcgcc | 960 |
| tcggggcgg gtattgccgc cccagccggg gccccggggg tcgccccctcc gcgcccaggc | 1020 |
| ggccgccaga ccagcggcgg cgaccacaag gccctcagta cctccggaga ggacaccctg | 1080 |
| agcgattcag atgatgaaga tgatgaagag gaagatgaag aggaagaaat cgacgtggtc | 1140 |
| actgtggaga agcggcgttc ctcctccaac accaaggctg tcaccacatt caccatcact | 1200 |
| gtgcgtccca gaacgcagc cctgggtccc gggagggctc agtccagcga gctgatcctc | 1260 |
| aaacgatgcc ttcccatcca ccagcagcac aactatgccg ccccctctcc ctacgtggag | 1320 |
| agtgaggatg caccccaca gaagaagata aagagcgagg cgtccccacg tccgctcaag | 1380 |
| agtgtcatcc ccccaaaggc taagagcttg agccccgaa actctgactc ggaggacagt | 1440 |
| gagcgtcgca gaaaccacaa catcctggag cgccagcgcc gcaacgacct tcggtccagc | 1500 |
| tttctcacgc tcagggacca cgtgccggag ttggtaaaga atgagaaggc cgccaaggtg | 1560 |
| gtcattttga aaaaggccac tgagtatgtc cactccctcc aggccgagga gcaccagctt | 1620 |
| ttgctggaaa aggaaaaatt gcaggcaaga cagcagcagt gctaaagaa aattgaacac | 1680 |
| gctcggactt gctagacgct tctcaaaact ggacagtcac tgccactttg cacattttga | 1740 |
| ttttttttt aaacaaacat tgtgttgaca ttaagaatgt tggtttactt tcaaatcggt | 1800 |

```
cccctgtcga gttcggctct gggtgggcag taggaccacc agtgtggggt tctgctggga    1860
ccttggagag cctgcatccc aggatgctgg gtggccctgc agcctcctcc acctcacctc    1920
catgacagcg ctaaacgttg gtgacggttg ggagcctctg gggctgttga agtcaccttg    1980
tgtgttccaa gtttccaaac aacagaaagt cattccttct ttttaaaatg gtgcttaagt    2040
tccagcagat gccacataag gggtttgcca tttgataccc ctggggaaca tttctgtaaa    2100
taccattgac acatccgcct tttgtataca tcctgggtaa tgagaggtgg cttttgcggc    2160
cagtattaga ctggaagttc atacctaagt actgtaataa tacctcaatg tttgaggagc    2220
atgttttgta tacaaatata ttgttaatct ctgttatgta ctgtactaat tcttacactg    2280
cctgtatact ttagtatgac gctgatacat aactaaattt gatacttata ttttcgtatg    2340
aaaatgagtt gtgaaagttt tgagtagata ttactttatc acttttttgaa ctaagaaact    2400 tttgtaaaga aatttactat atatatatgc cttttttccta gcctgtttct tcctgttaat    2460
gtatttgttc atgtttggtg catagaactg ggtaaatgca aagttctgtg tttaatttct    2520
tcaaaatgta tatatttagt gctgcatctt atagcacttt gaaataccctc atgtttatga    2580 aaataaatag cttaaaatta aatgaaaaaa aaa                                   2613
```

```
<210> SEQ ID NO 3
<211> LENGTH: 16
<212> TYPE: DNA
<213> ORGANISM: Homo sapiens

<400> SEQUENCE: 3
agttcctgtt ggtgaa                                                       16

<210> SEQ ID NO 4
<211> LENGTH: 16
<212> TYPE: DNA
<213> ORGANISM: Homo sapiens

<400> SEQUENCE: 4
tcaccatgtc tcctcc                                                       16

<210> SEQ ID NO 5
<211> LENGTH: 16
<212> TYPE: DNA
<213> ORGANISM: Homo sapiens

<400> SEQUENCE: 5
ttcaccatgt ctcctc                                                       16

<210> SEQ ID NO 6
<211> LENGTH: 16
<212> TYPE: DNA
<213> ORGANISM: Homo sapiens

<400> SEQUENCE: 6
ggttcaccat gtctcc                                                       16

<210> SEQ ID NO 7
<211> LENGTH: 16
<212> TYPE: DNA
<213> ORGANISM: Homo sapiens

<400> SEQUENCE: 7
tacagtcctg gatgat                                                       16
```

```
<210> SEQ ID NO 8
<211> LENGTH: 16
<212> TYPE: DNA
<213> ORGANISM: Homo sapiens

<400> SEQUENCE: 8
catacagtcc tggatg                                                     16

<210> SEQ ID NO 9
<211> LENGTH: 16
<212> TYPE: DNA
<213> ORGANISM: Homo sapiens

<400> SEQUENCE: 9
tgttggtgaa gctaac                                                     16

<210> SEQ ID NO 10
<211> LENGTH: 16
<212> TYPE: DNA
<213> ORGANISM: Homo sapiens

<400> SEQUENCE: 10
ctgttggtga agctaa                                                     16

<210> SEQ ID NO 11
<211> LENGTH: 16
<212> TYPE: DNA
<213> ORGANISM: Homo sapiens

<400> SEQUENCE: 11
ggtacaagct ggaggt                                                     16

<210> SEQ ID NO 12
<211> LENGTH: 16
<212> TYPE: DNA
<213> ORGANISM: Homo sapiens

<400> SEQUENCE: 12
gtgaggaggt ttgctg                                                     16

<210> SEQ ID NO 13
<211> LENGTH: 16
<212> TYPE: DNA
<213> ORGANISM: Homo sapiens

<400> SEQUENCE: 13
tgtgaggagg tttgct                                                     16

<210> SEQ ID NO 14
<211> LENGTH: 16
<212> TYPE: DNA
<213> ORGANISM: Homo sapiens

<400> SEQUENCE: 14
tagttgtgct gatgtg                                                     16

<210> SEQ ID NO 15
<211> LENGTH: 16
<212> TYPE: DNA
<213> ORGANISM: Homo sapiens

<400> SEQUENCE: 15
gtagttgtgc tgatgt                                                     16
```

```
<210> SEQ ID NO 16
<211> LENGTH: 16
<212> TYPE: DNA
<213> ORGANISM: Homo sapiens

<400> SEQUENCE: 16
gacactgtcc aacttg                                                    16

<210> SEQ ID NO 17
<211> LENGTH: 16
<212> TYPE: DNA
<213> ORGANISM: Homo sapiens

<400> SEQUENCE: 17
tcaggactct gacact                                                    16

<210> SEQ ID NO 18
<211> LENGTH: 16
<212> TYPE: DNA
<213> ORGANISM: Homo sapiens

<400> SEQUENCE: 18
ctcaggactc tgacac                                                    16

<210> SEQ ID NO 19
<211> LENGTH: 16
<212> TYPE: DNA
<213> ORGANISM: Homo sapiens

<400> SEQUENCE: 19
atctgtctca ggactc                                                    16

<210> SEQ ID NO 20
<211> LENGTH: 16
<212> TYPE: DNA
<213> ORGANISM: Homo sapiens

<400> SEQUENCE: 20
gatctgtctc aggact                                                    16

<210> SEQ ID NO 21
<211> LENGTH: 16
<212> TYPE: DNA
<213> ORGANISM: Homo sapiens

<400> SEQUENCE: 21
tgatctgtct caggac                                                    16

<210> SEQ ID NO 22
<211> LENGTH: 16
<212> TYPE: DNA
<213> ORGANISM: Homo sapiens

<400> SEQUENCE: 22
aggataacta ccttgg                                                    16

<210> SEQ ID NO 23
<211> LENGTH: 16
<212> TYPE: DNA
<213> ORGANISM: Homo sapiens

<400> SEQUENCE: 23
gacaggatgt atgctg                                                    16
```

<210> SEQ ID NO 24
<211> LENGTH: 16
<212> TYPE: DNA
<213> ORGANISM: Homo sapiens

<400> SEQUENCE: 24
ggacaggatg tatgct                                                    16

<210> SEQ ID NO 25
<211> LENGTH: 16
<212> TYPE: DNA
<213> ORGANISM: Homo sapiens

<400> SEQUENCE: 25
gctgttcaag tttgtg                                                    16

<210> SEQ ID NO 26
<211> LENGTH: 16
<212> TYPE: DNA
<213> ORGANISM: Homo sapiens
<220> FEATURE:
<221> NAME/KEY: misc_feature
<222> LOCATION: (1)..(3)
<223> OTHER INFORMATION: nucleoside analogue monomer
<220> FEATURE:
<221> NAME/KEY: misc_feature
<222> LOCATION: (1)..(16)
<223> OTHER INFORMATION: phosphorothioate linkage groups between
      monomers
<220> FEATURE:
<221> NAME/KEY: misc_feature
<222> LOCATION: (14)..(16)
<223> OTHER INFORMATION: nucleoside analogue monomer

<400> SEQUENCE: 26
agttcctgtt ggtgaa                                                    16

<210> SEQ ID NO 27
<211> LENGTH: 16
<212> TYPE: DNA
<213> ORGANISM: Homo sapiens
<220> FEATURE:
<221> NAME/KEY: misc_feature
<222> LOCATION: (1)..(3)
<223> OTHER INFORMATION: nucleoside analogue monomer
<220> FEATURE:
<221> NAME/KEY: misc_feature
<222> LOCATION: (1)..(16)
<223> OTHER INFORMATION: phosphorothioate linkage group between monomers
<220> FEATURE:
<221> NAME/KEY: modified_base
<222> LOCATION: (2)..(2)
<223> OTHER INFORMATION: 5-methylcytosine base
<220> FEATURE:
<221> NAME/KEY: misc_feature
<222> LOCATION: (14)..(16)
<223> OTHER INFORMATION: nucleoside analogue monomer
<220> FEATURE:
<221> NAME/KEY: modified_base
<222> LOCATION: (15)..(16)
<223> OTHER INFORMATION: 5-methylcytosine base

<400> SEQUENCE: 27
tcaccatgtc tcctcc                                                    16

<210> SEQ ID NO 28
<211> LENGTH: 16
<212> TYPE: DNA
<213> ORGANISM: Homo sapiens

```
<220> FEATURE:
<221> NAME/KEY: misc_feature
<222> LOCATION: (1)..(3)
<223> OTHER INFORMATION: nucleoside analogue monomer
<220> FEATURE:
<221> NAME/KEY: misc_feature
<222> LOCATION: (1)..(16)
<223> OTHER INFORMATION: phosphorothioate group linkage between monomers
<220> FEATURE:
<221> NAME/KEY: modified_base
<222> LOCATION: (3)..(3)
<223> OTHER INFORMATION: 5-methylcytosine base
<220> FEATURE:
<221> NAME/KEY: modified_base
<222> LOCATION: (14)..(14)
<223> OTHER INFORMATION: 5-methylcytosine base
<220> FEATURE:
<221> NAME/KEY: misc_feature
<222> LOCATION: (14)..(16)
<223> OTHER INFORMATION: nucleoside analogue monomer
<220> FEATURE:
<221> NAME/KEY: modified_base
<222> LOCATION: (16)..(16)
<223> OTHER INFORMATION: 5-methylcytosine base

<400> SEQUENCE: 28
ttcaccatgt ctcctc                                                     16

<210> SEQ ID NO 29
<211> LENGTH: 16
<212> TYPE: DNA
<213> ORGANISM: Homo sapiens
<220> FEATURE:
<221> NAME/KEY: misc_feature
<222> LOCATION: (1)..(3)
<223> OTHER INFORMATION: nucleoside analogue monomer
<220> FEATURE:
<221> NAME/KEY: misc_feature
<222> LOCATION: (1)..(16)
<223> OTHER INFORMATION: phosphorothioate linkage group between monomers
<220> FEATURE:
<221> NAME/KEY: misc_feature
<222> LOCATION: (14)..(16)
<223> OTHER INFORMATION: nucleoside analogue monomer
<220> FEATURE:
<221> NAME/KEY: modified_base
<222> LOCATION: (15)..(16)
<223> OTHER INFORMATION: 5-methylcytosine base

<400> SEQUENCE: 29
ggttcaccat gtctcc                                                     16

<210> SEQ ID NO 30
<211> LENGTH: 16
<212> TYPE: DNA
<213> ORGANISM: Homo sapiens
<220> FEATURE:
<221> NAME/KEY: misc_feature
<222> LOCATION: (1)..(3)
<223> OTHER INFORMATION: nucleoside analogue monomer
<220> FEATURE:
<221> NAME/KEY: misc_feature
<222> LOCATION: (1)..(16)
<223> OTHER INFORMATION: phosphorothioage linkage group between monomers
<220> FEATURE:
<221> NAME/KEY: modified_base
<222> LOCATION: (3)..(3)
<223> OTHER INFORMATION: 5-methylcytosine base
<220> FEATURE:
<221> NAME/KEY: misc_feature
<222> LOCATION: (14)..(16)
<223> OTHER INFORMATION: nucleoside analogue monomer

<400> SEQUENCE: 30
```

```
tacagtcctg gatgat                                                          16

<210> SEQ ID NO 31
<211> LENGTH: 16
<212> TYPE: DNA
<213> ORGANISM: Homo sapiens
<220> FEATURE:
<221> NAME/KEY: misc_feature
<222> LOCATION: (1)..(3)
<223> OTHER INFORMATION: nucleoside analogue monomer
<220> FEATURE:
<221> NAME/KEY: modified_base
<222> LOCATION: (1)..(1)
<223> OTHER INFORMATION: 5-methylcytosine base
<220> FEATURE:
<221> NAME/KEY: misc_feature
<222> LOCATION: (1)..(16)
<223> OTHER INFORMATION: phosphorothioate linkage group between  monomers
<220> FEATURE:
<221> NAME/KEY: misc_feature
<222> LOCATION: (14)..(16)
<223> OTHER INFORMATION: nucleoside analogue monomer

<400> SEQUENCE: 31
catacagtcc tggatg                                                          16

<210> SEQ ID NO 32
<211> LENGTH: 16
<212> TYPE: DNA
<213> ORGANISM: Homo sapiens
<220> FEATURE:
<221> NAME/KEY: misc_feature
<222> LOCATION: (1)..(3)
<223> OTHER INFORMATION: nucleoside analogue monomer
<220> FEATURE:
<221> NAME/KEY: misc_feature
<222> LOCATION: (1)..(16)
<223> OTHER INFORMATION: phosphorothioate linkage group between monomers
<220> FEATURE:
<221> NAME/KEY: misc_feature
<222> LOCATION: (14)..(16)
<223> OTHER INFORMATION: nucleoside analogue monomer
<220> FEATURE:
<221> NAME/KEY: modified_base
<222> LOCATION: (16)..(16)
<223> OTHER INFORMATION: 5-methylcytosine base

<400> SEQUENCE: 32
tgttggtgaa gctaac                                                          16

<210> SEQ ID NO 33
<211> LENGTH: 16
<212> TYPE: DNA
<213> ORGANISM: Homo sapiens
<220> FEATURE:
<221> NAME/KEY: misc_feature
<222> LOCATION: (1)..(3)
<223> OTHER INFORMATION: nucleoside analogue monomer
<220> FEATURE:
<221> NAME/KEY: modified_base
<222> LOCATION: (1)..(1)
<223> OTHER INFORMATION: 5-methylcytosine base
<220> FEATURE:
<221> NAME/KEY: misc_feature
<222> LOCATION: (1)..(16)
<223> OTHER INFORMATION: phosphorothioate linkage group between monomers
<220> FEATURE:
<221> NAME/KEY: misc_feature
<222> LOCATION: (14)..(16)
<223> OTHER INFORMATION: nucleoside analogue monomer

<400> SEQUENCE: 33
ctgttggtga agctaa                                                          16
```

```
<210> SEQ ID NO 34
<211> LENGTH: 16
<212> TYPE: DNA
<213> ORGANISM: Homo sapiens
<220> FEATURE:
<221> NAME/KEY: misc_feature
<222> LOCATION: (1)..(3)
<223> OTHER INFORMATION: nucleoside analogue monomer
<220> FEATURE:
<221> NAME/KEY: misc_feature
<222> LOCATION: (1)..(16)
<223> OTHER INFORMATION: phosphorothioate linkage group between monomers
<220> FEATURE:
<221> NAME/KEY: misc_feature
<222> LOCATION: (14)..(16)
<223> OTHER INFORMATION: nucleoside analogue monomer

<400> SEQUENCE: 34
ggtacaagct ggaggt                                                    16

<210> SEQ ID NO 35
<211> LENGTH: 16
<212> TYPE: DNA
<213> ORGANISM: Homo sapiens
<220> FEATURE:
<221> NAME/KEY: misc_feature
<222> LOCATION: (1)..(3)
<223> OTHER INFORMATION: nucleoside analogue monomer
<220> FEATURE:
<221> NAME/KEY: misc_feature
<222> LOCATION: (1)..(16)
<223> OTHER INFORMATION: phosphorothioate linkage group between monomers
<220> FEATURE:
<221> NAME/KEY: modified_base
<222> LOCATION: (14)..(14)
<223> OTHER INFORMATION: 5-methylcytosine base
<220> FEATURE:
<221> NAME/KEY: misc_feature
<222> LOCATION: (14)..(16)
<223> OTHER INFORMATION: nucleoside analogue monomer

<400> SEQUENCE: 35
gtgaggaggt ttgctg                                                    16

<210> SEQ ID NO 36
<211> LENGTH: 16
<212> TYPE: DNA
<213> ORGANISM: Homo sapiens
<220> FEATURE:
<221> NAME/KEY: misc_feature
<222> LOCATION: (1)..(3)
<223> OTHER INFORMATION: nucleoside analogue monomer
<220> FEATURE:
<221> NAME/KEY: misc_feature
<222> LOCATION: (1)..(16)
<223> OTHER INFORMATION: phosphorothioate linkage group between monomers
<220> FEATURE:
<221> NAME/KEY: misc_feature
<222> LOCATION: (14)..(16)
<223> OTHER INFORMATION: nucleoside analogue monomer
<220> FEATURE:
<221> NAME/KEY: modified_base
<222> LOCATION: (15)..(15)
<223> OTHER INFORMATION: 5-methylcytosine base

<400> SEQUENCE: 36
tgtgaggagg tttgct                                                    16

<210> SEQ ID NO 37
<211> LENGTH: 16
<212> TYPE: DNA
```

```
<213> ORGANISM: Homo sapiens
<220> FEATURE:
<221> NAME/KEY: misc_feature
<222> LOCATION: (1)..(3)
<223> OTHER INFORMATION: nucleoside analogue monomer
<220> FEATURE:
<221> NAME/KEY: misc_feature
<222> LOCATION: (1)..(16)
<223> OTHER INFORMATION: phosphorothioate linkage group between monomers
<220> FEATURE:
<221> NAME/KEY: misc_feature
<222> LOCATION: (14)..(16)
<223> OTHER INFORMATION: nucleoside analogue monomer

<400> SEQUENCE: 37
tagttgtgct gatgtg                                            16

<210> SEQ ID NO 38
<211> LENGTH: 16
<212> TYPE: DNA
<213> ORGANISM: Homo sapiens
<220> FEATURE:
<221> NAME/KEY: misc_feature
<222> LOCATION: (1)..(3)
<223> OTHER INFORMATION: nucleoside analogue monomer
<220> FEATURE:
<221> NAME/KEY: misc_feature
<222> LOCATION: (1)..(16)
<223> OTHER INFORMATION: phosphorothioate linkage group between monomers
<220> FEATURE:
<221> NAME/KEY: misc_feature
<222> LOCATION: (14)..(16)
<223> OTHER INFORMATION: nucleoside analogue monomer

<400> SEQUENCE: 38
gtagttgtgc tgatgt                                            16

<210> SEQ ID NO 39
<211> LENGTH: 16
<212> TYPE: DNA
<213> ORGANISM: Homo sapiens
<220> FEATURE:
<221> NAME/KEY: misc_feature
<222> LOCATION: (1)..(3)
<223> OTHER INFORMATION: nucleoside analogue monomer
<220> FEATURE:
<221> NAME/KEY: misc_feature
<222> LOCATION: (1)..(16)
<223> OTHER INFORMATION: phosphorothioate linkage group between monomers
<220> FEATURE:
<221> NAME/KEY: modified_base
<222> LOCATION: (3)..(3)
<223> OTHER INFORMATION: 5-methylcytosine base
<220> FEATURE:
<221> NAME/KEY: misc_feature
<222> LOCATION: (14)..(16)
<223> OTHER INFORMATION: nucleoside analogue monomer

<400> SEQUENCE: 39
gacactgtcc aacttg                                            16

<210> SEQ ID NO 40
<211> LENGTH: 16
<212> TYPE: DNA
<213> ORGANISM: Homo sapiens
<220> FEATURE:
<221> NAME/KEY: misc_feature
<222> LOCATION: (1)..(3)
<223> OTHER INFORMATION: nucleoside analogue monomer
<220> FEATURE:
<221> NAME/KEY: misc_feature
<222> LOCATION: (1)..(16)
<223> OTHER INFORMATION: phosphorothioate linkage group between monomers
```

-continued

```
<220> FEATURE:
<221> NAME/KEY: modified_base
<222> LOCATION: (2)..(2)
<223> OTHER INFORMATION: 5-methylcytosine base
<220> FEATURE:
<221> NAME/KEY: misc_feature
<222> LOCATION: (14)..(16)
<223> OTHER INFORMATION: nucleoside analogue monomer
<220> FEATURE:
<221> NAME/KEY: modified_base
<222> LOCATION: (15)..(15)
<223> OTHER INFORMATION: 5-methylcytosine base

<400> SEQUENCE: 40
tcaggactct gacact                                                   16

<210> SEQ ID NO 41
<211> LENGTH: 16
<212> TYPE: DNA
<213> ORGANISM: Homo sapiens
<220> FEATURE:
<221> NAME/KEY: misc_feature
<222> LOCATION: (1)..(3)
<223> OTHER INFORMATION: nucleoside analogue monomer
<220> FEATURE:
<221> NAME/KEY: modified_base
<222> LOCATION: (1)..(1)
<223> OTHER INFORMATION: 5-methylcytosine base
<220> FEATURE:
<221> NAME/KEY: misc_feature
<222> LOCATION: (1)..(16)
<223> OTHER INFORMATION: phosphorothioate linkage group between monomers
<220> FEATURE:
<221> NAME/KEY: modified_base
<222> LOCATION: (3)..(3)
<223> OTHER INFORMATION: 5-methylcytosine base
<220> FEATURE:
<221> NAME/KEY: modified_base
<222> LOCATION: (14)..(14)
<223> OTHER INFORMATION: 5-methylcytosine base
<220> FEATURE:
<221> NAME/KEY: misc_feature
<222> LOCATION: (14)..(16)
<223> OTHER INFORMATION: nucleoside analogue monomer
<220> FEATURE:
<221> NAME/KEY: modified_base
<222> LOCATION: (16)..(16)
<223> OTHER INFORMATION: 5-methylcytosine base

<400> SEQUENCE: 41
ctcaggactc tgacac                                                   16

<210> SEQ ID NO 42
<211> LENGTH: 16
<212> TYPE: DNA
<213> ORGANISM: Homo sapiens
<220> FEATURE:
<221> NAME/KEY: misc_feature
<222> LOCATION: (1)..(3)
<223> OTHER INFORMATION: nucleoside analogue monomer
<220> FEATURE:
<221> NAME/KEY: misc_feature
<222> LOCATION: (1)..(16)
<223> OTHER INFORMATION: phosphorothioate linkage group between monomers
<220> FEATURE:
<221> NAME/KEY: modified_base
<222> LOCATION: (3)..(3)
<223> OTHER INFORMATION: 5-methylcytosine base
<220> FEATURE:
<221> NAME/KEY: modified_base
<222> LOCATION: (14)..(14)
<223> OTHER INFORMATION: 5-methylcytosine base
<220> FEATURE:
<221> NAME/KEY: misc_feature
<222> LOCATION: (14)..(16)
```

<223> OTHER INFORMATION: nucleoside analogue monomer
<220> FEATURE:
<221> NAME/KEY: modified_base
<222> LOCATION: (16)..(16)
<223> OTHER INFORMATION: 5-methylcytosine base

<400> SEQUENCE: 42
atctgtctca ggactc                                                    16

<210> SEQ ID NO 43
<211> LENGTH: 16
<212> TYPE: DNA
<213> ORGANISM: Homo sapiens
<220> FEATURE:
<221> NAME/KEY: misc_feature
<222> LOCATION: (1)..(3)
<223> OTHER INFORMATION: nucleoside analogue monomer
<220> FEATURE:
<221> NAME/KEY: misc_feature
<222> LOCATION: (1)..(16)
<223> OTHER INFORMATION: phosphorothioate linkage group between monomers
<220> FEATURE:
<221> NAME/KEY: misc_feature
<222> LOCATION: (14)..(16)
<223> OTHER INFORMATION: nucleoside analogue monomer
<220> FEATURE:
<221> NAME/KEY: modified_base
<222> LOCATION: (15)..(15)
<223> OTHER INFORMATION: 5-methylcytosine base

<400> SEQUENCE: 43
gatctgtctc aggact                                                    16

<210> SEQ ID NO 44
<211> LENGTH: 16
<212> TYPE: DNA
<213> ORGANISM: Homo sapiens
<220> FEATURE:
<221> NAME/KEY: misc_feature
<222> LOCATION: (1)..(3)
<223> OTHER INFORMATION: nucleoside analogue monomer
<220> FEATURE:
<221> NAME/KEY: misc_feature
<222> LOCATION: (1)..(16)
<223> OTHER INFORMATION: phosphorothioate linkage group between monomers
<220> FEATURE:
<221> NAME/KEY: misc_feature
<222> LOCATION: (14)..(16)
<223> OTHER INFORMATION: nucleoside analogue monomer
<220> FEATURE:
<221> NAME/KEY: modified_base
<222> LOCATION: (16)..(16)
<223> OTHER INFORMATION: 5-methylcytosine base

<400> SEQUENCE: 44
tgatctgtct caggac                                                    16

<210> SEQ ID NO 45
<211> LENGTH: 16
<212> TYPE: DNA
<213> ORGANISM: Homo sapiens
<220> FEATURE:
<221> NAME/KEY: misc_feature
<222> LOCATION: (1)..(3)
<223> OTHER INFORMATION: nucleoside analogue monomer
<220> FEATURE:
<221> NAME/KEY: misc_feature
<222> LOCATION: (1)..(16)
<223> OTHER INFORMATION: phosphorothioate linkage group between monomers
<220> FEATURE:
<221> NAME/KEY: misc_feature
<222> LOCATION: (14)..(16)
<223> OTHER INFORMATION: nucleoside analogue monomer -continued

<400> SEQUENCE: 45
aggataacta ccttgg                                                          16

<210> SEQ ID NO 46
<211> LENGTH: 16
<212> TYPE: DNA
<213> ORGANISM: Homo sapiens
<220> FEATURE:
<221> NAME/KEY: misc_feature
<222> LOCATION: (1)..(3)
<223> OTHER INFORMATION: nucleoside analogue monomer
<220> FEATURE:
<221> NAME/KEY: misc_feature
<222> LOCATION: (1)..(16)
<223> OTHER INFORMATION: phosphorothioate linkage group between monomers
<220> FEATURE:
<221> NAME/KEY: modified_base
<222> LOCATION: (3)..(3)
<223> OTHER INFORMATION: 5-methylcytosine base
<220> FEATURE:
<221> NAME/KEY: modified_base
<222> LOCATION: (14)..(14)
<223> OTHER INFORMATION: 5-methylcytosine base
<220> FEATURE:
<221> NAME/KEY: misc_feature
<222> LOCATION: (14)..(16)
<223> OTHER INFORMATION: nucleoside analogue monomer

<400> SEQUENCE: 46
gacaggatgt atgctg                                                          16

<210> SEQ ID NO 47
<211> LENGTH: 16
<212> TYPE: DNA
<213> ORGANISM: Homo sapiens
<220> FEATURE:
<221> NAME/KEY: misc_feature
<222> LOCATION: (1)..(3)
<223> OTHER INFORMATION: nucleoside analogue monomer
<220> FEATURE:
<221> NAME/KEY: misc_feature
<222> LOCATION: (1)..(16)
<223> OTHER INFORMATION: phosphorothioate linkage group between monomers
<220> FEATURE:
<221> NAME/KEY: misc_feature
<222> LOCATION: (14)..(16)
<223> OTHER INFORMATION: nucleoside analogue monomer
<220> FEATURE:
<221> NAME/KEY: modified_base
<222> LOCATION: (15)..(15)
<223> OTHER INFORMATION: 5-methylcytosine base

<400> SEQUENCE: 47
ggacaggatg tatgct                                                          16

<210> SEQ ID NO 48
<211> LENGTH: 16
<212> TYPE: DNA
<213> ORGANISM: Homo sapiens
<220> FEATURE:
<221> NAME/KEY: misc_feature
<222> LOCATION: (1)..(3)
<223> OTHER INFORMATION: nucleoside analogue monomer
<220> FEATURE:
<221> NAME/KEY: misc_feature
<222> LOCATION: (1)..(16)
<223> OTHER INFORMATION: phosphorothioate linkage group between monomers
<220> FEATURE:
<221> NAME/KEY: modified_base
<222> LOCATION: (2)..(2)
<223> OTHER INFORMATION: 5-methylcytosine base
<220> FEATURE:

```
<221> NAME/KEY: misc_feature
<222> LOCATION: (14)..(16)
<223> OTHER INFORMATION: nucleoside analogue monomer

<400> SEQUENCE: 48
gctgttcaag tttgtg                                               16
```

LNA ANTISENSE OLIGONUCLEOTIDES FOR THE MODULATION OF MYC EXPRESSION

STATEMENT REGARDING FEDERALLY SPONSORED RESEARCH

This invention was made with government support under grant number K08CA128972 awarded by The National Institutes of Health. The government has certain rights in the invention.

FIELD OF THE INVENTION

The present disclosure provides compositions and methods for modulating the expression of members of the Myc transcription factor family. In particular, this disclosure relates to oligonucleotides, including LNA nucleotides, which are specifically hybridizable with nucleic acids encoding Myc transcription family members. The LNA oligonucleotides disclosed herein have been shown to modulate the expression of c-Myc. Pharmaceutical preparations thereof and their use as treatment of cancer diseases are also disclosed.

BACKGROUND

The Myc regulator genes encode a family of transcription factors involved in cell proliferation, growth, differentiation and apoptosis. Members of the Myc transcription factor family include c-Myc, N-Myc and L-Myc. Myc proteins activate expression of many genes through binding of consensus sequences (Enhancer Box sequences (E-boxes)) and recruiting histone acetyltransferases. Activation of normal Myc genes affects numerous cellular processes, including cell cycle progression, cell growth and division, metabolism, telomerase activity, adhesion and motility, angiogenesis and differentiation.

Myc is also a very strong proto-oncogene and mutated versions are often found to be upregulated and/or constitutively expressed in many types of cancers. Many hematological and solid tumor malignancies have been found to possess aberrations in one or more Myc genes. The major genetic Myc aberrations found in human tumors include gene amplification in solid tumors and chromosome translocation in lymphoma and leukemia.

Myc-dependent cancers cells do not survive in the absence of Myc. Many researchers have attempted to exploit this vulnerability by developing chemotherapeutic agents targeting Myc. However, attempts at designing effective small molecule inhibitors of Myc have been unsuccessful because the proteins are small and do not provide good binding sites for chemotherapeutic agents.

Accordingly, there is a need for new classes of chemotherapeutic agents that target and efficiently downregulate Myc.

SUMMARY

The present disclosure provides an oligomer having a sequence selected from the group consisting of SEQ ID NOs: 3-48, wherein the sequence is at least 80%, at least 85%, at least 90%, at least 95%, at least 98% or at least 100% identical to the reverse complement of a target region of a nucleic acid which encodes a mammalian Myc transcription factor, such as a mammalian Myc gene or mRNA, such as a nucleic acid having the sequence set forth in SEQ ID NO: 1, or the sequence set forth in SEQ ID NO: 2, or naturally occurring variants thereof. Thus, for example, the oligomer hybridizes to a region of a single-stranded nucleic acid molecule having the sequence shown in SEQ ID NO: 1 or SEQ ID NO: 2.

The disclosure provides for a conjugate comprising the oligomer according to the disclosure, and at least one non-nucleotide or non-polynucleotide moiety covalently attached to the oligomer.

The disclosure provides for a pharmaceutical composition comprising the oligomer or the conjugate according to the disclosure, and a pharmaceutically acceptable diluent, carrier, salt or adjuvant.

The present disclosure further provides for a method of inhibiting Myc expression, the method comprising administering an effective amount of an oligomer, or a conjugate according to the disclosure, to the cell so as to effect the inhibition of Myc expression in said cell. The disclosure further provides for a method of inhibiting Myc in the tissue of a mammal, comprising contacting the tissue with an effective amount of an oligomer or a conjugate of the disclosure. In certain embodiments the Myc is c-Myc. In other embodiments, the Myc is N-Myc. In various embodiments, the Myc is c-Myc and/or N-Myc.

The disclosure provides for a method of treating a disease or disorder as disclosed herein, such as a hyperproliferative disorder, such as cancer, the method comprising administering an oligomer, a conjugate, or a pharmaceutical composition according to the disclosure as a therapeutic to a patient suffering from the disease or disorder or as a prophylactic to a patient susceptible to the disease or disorder.

DETAILED DESCRIPTION

1. The Oligomer

Figure 1A:
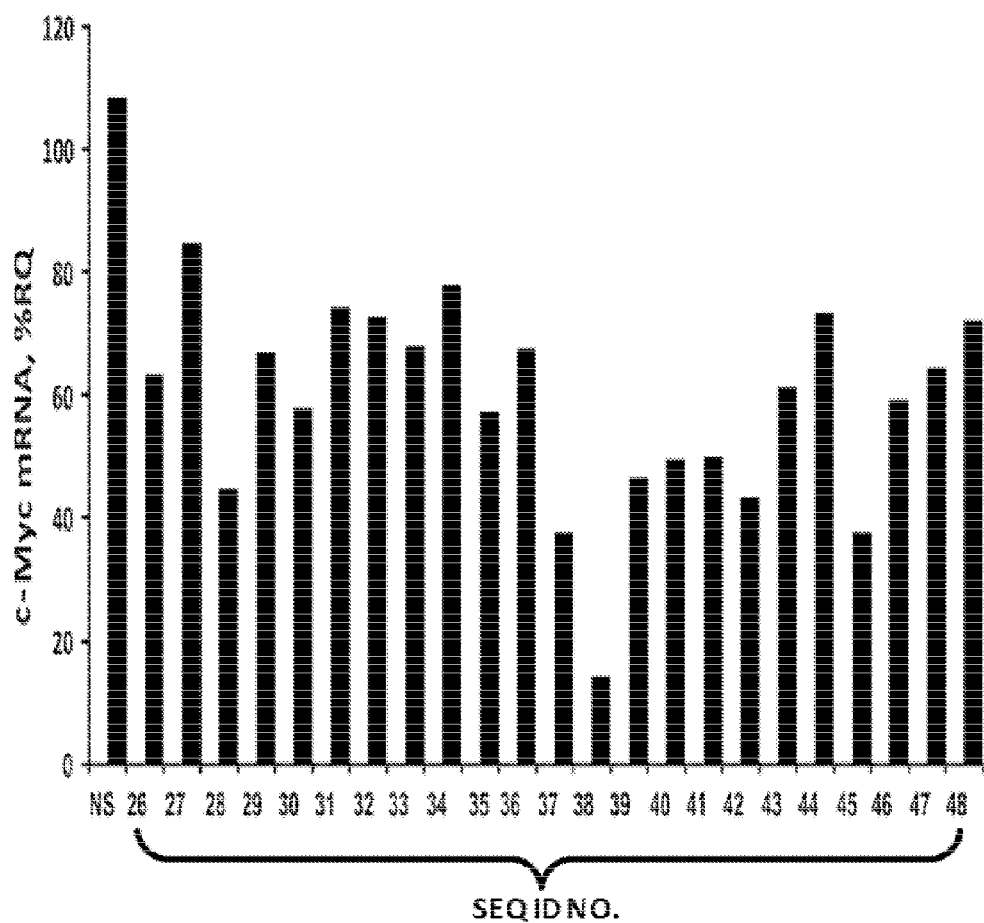
FIG. 1A is a graph showing c-Myc mRNA down regulation in MM1.S multiple myeloma cells in response to the LNA oligomers represented by SEQ ID NOs: 26-48.

The present disclosure employs oligomeric compounds (referred herein as oligomers) for use in modulating the function of nucleic acid molecules encoding a mammalian transcription factor Myc, such as the c-Myc nucleic acid (SEQ ID NO: 1), and other naturally occurring members of the Myc family, such as N-Myc (SEQ ID NO: 2). In certain embodiments, the nucleic acid molecules encode human Myc. In other embodiments, the nucleic acid molecules encode mouse Myc. In still other embodiments, the nucleic acid molecules encode monkey Myc or chimpanzee Myc. As used herein, the term "Myc" refers collectively to the Myc family of transcription factors, including c-Myc, N-Myc, and L-Myc. The term "oligomer" as used herein refers to a molecule formed by covalent linkage of two or more monomers (i.e. an oligonucleotide). In some embodiments, the oligomer comprises or consists of from 10-30 covalently linked monomers.

The term "monomer" includes both nucleosides and deoxynucleosides (collectively, "nucleosides") that occur naturally in nucleic acids and that do not contain either modified sugars or modified nucleobases, i.e., compounds in which a ribose sugar or deoxyribose sugar is covalently bonded to a naturally-occurring, unmodified nucleobase (base) moiety (i.e., the purine and pyrimidine heterocycles adenine, guanine, cytosine, thymine or uracil) and "nucleoside analogues," which are nucleosides that either do occur naturally in nucleic acids or do not occur naturally in nucleic acids, wherein either the sugar moiety is other than a ribose or a deoxyribose sugar (such as bicyclic sugars or 2' modified sugars, such as 2' substituted sugars), or the base moiety is modified (e.g., 5-methylcytosine), or both.

An "RNA monomer" is a nucleoside containing a ribose sugar and an unmodified nucleobase.

A "DNA monomer" is a nucleoside containing a deoxyribose sugar and an unmodified nucleobase.

A "Locked Nucleic Acid monomer," "locked monomer," or "LNA monomer" is a nucleoside analogue having a bicyclic sugar, as further described herein below.

The terms "corresponding nucleoside analogue" and "corresponding nucleoside" indicate that the base moiety in the nucleoside analogue and the base moiety in the nucleoside are identical. For example, when the "nucleoside" contains a 2-deoxyribose sugar linked to an adenine, the "corresponding nucleoside analogue" contains, for example, a modified sugar linked to an adenine base moiety.

The terms "oligomer," "oligomeric compound," and "oligonucleotide" are used interchangeably in the context of the disclosure, and refer to a molecule formed by covalent linkage of two or more contiguous monomers by, for example, a phosphate group (forming a phosphodiester linkage between nucleosides) or a phosphorothioate group (forming a phosphorothioate linkage between nucleosides). The oligomer consists of, or comprises, 10-50 monomers, such as 10-30 monomers.

In some embodiments, an oligomer comprises nucleosides, or nucleoside analogues, or mixtures thereof as referred to herein. An "LNA oligomer" or "LNA oligonucleotide" refers to an oligonucleotide containing one or more LNA monomers.

Nucleoside analogues that are optionally included within oligomers may function similarly to corresponding nucleosides, or may have specific improved functions. Oligomers wherein some or all of the monomers are nucleoside analogues are often preferred over native forms because of several desirable properties of such oligomers, such as the ability to penetrate a cell membrane, good resistance to extra- and/or intracellular nucleases and high affinity and specificity for the nucleic acid target. LNA monomers are particularly preferred, for example, for conferring several of the above-mentioned properties.

In various embodiments, one or more nucleoside analogues present within the oligomer are "silent" or "equivalent" in function to the corresponding natural nucleoside, i.e., have no functional effect on the way the oligomer functions to inhibit target gene expression. Such "equivalent" nucleoside analogues are nevertheless useful if, for example, they are easier or cheaper to manufacture, or are more stable under storage or manufacturing conditions, or can incorporate a tag or label. Typically, however, the analogues will have a functional effect on the way in which the oligomer functions to inhibit expression; for example, by producing increased binding affinity to the target region of the target nucleic acid and/or increased resistance to intracellular nucleases and/or increased ease of transport into the cell.

Thus, in various embodiments, oligomers according to the disclosure comprise nucleoside monomers and at least one nucleoside analogue monomer, such as an LNA monomer, or other nucleoside analogue monomers.

The term "at least one" comprises the integers larger than or equal to 1, such as 1, 2, 3, 4, 5, 6, 7, 8, 9, 10, 11, 12, 13, 14, 15, 16, 17, 18, 19, 20 and so forth. In various embodiments, such as when referring to the nucleic acid or protein targets of the compounds of the disclosure, the term "at least one" includes the terms "at least two" and "at least three" and "at least four." Likewise, in some embodiments, the term "at least two" comprises the terms "at least three" and "at least four."

In some embodiments, the oligomer comprises or consists of 10, 11, 12, 13, 14, 15, 16, 17, 18, 19, 20, 21, 22, 23, 24, 25, 26, 27, 28, 29 or 30 contiguous monomers.

In some embodiments, the oligomer comprises or consists of 10-22 contiguous monomers, such as 12-18 contiguous monomers, such as 13-17 or 12-16 contiguous monomers, such as 13, 14, 15, 16 contiguous monomers.

In certain embodiments, the oligomer comprises or consists of 10, 11, 12, 13, or 14 contiguous monomers.

In various embodiments, the oligomer according to the disclosure consists of no more than 22 monomers, such as no more than 20 monomers, such as no more than 18 monomers, such as 15, 16 or 17 monomers. In some embodiments, the oligomer comprises less than 20 monomers.

In various embodiments, the compounds do not comprise RNA monomers.

In various embodiments, the compounds are linear molecules or are linear as synthesized. In these embodiments, the oligomer is a single stranded molecule, and typically does not comprise short regions of, for example, at least 3, 4 or 5 contiguous monomers, which are complementary to another region within the same oligomer such that the oligomer forms an internal duplex. In some embodiments, the oligomer is essentially not double stranded, i.e., is not a siRNA.

In some embodiments, the oligomer of the disclosure consists of a contiguous stretch of monomers, the sequence of which is identified by a SEQ ID NO disclosed herein (see, e.g., Tables 1-3). In other embodiments, the oligomer comprises a first region, the region consisting of a contiguous stretch of monomers, and one or more additional regions which consist of at least one additional monomer. In some embodiments the first region is positioned 5' to the additional region, in others the first region is positioned 3' to the additional region, and in still other embodiments, the first region is flanked by one or more additional regions. In some embodiments, the sequence of the first region is identified by a SEQ ID NO disclosed herein.

2. Gapmer Design

Typically, the oligomer of the disclosure is a gapmer.

A "gapmer" is an oligomer which comprises a contiguous stretch of monomers capable of recruiting an RNAse (e.g., such as RNAseH) as further described herein below, such as a region of at least 6 or 7 DNA monomers, referred to herein as region B, wherein region B is flanked both on its 5' and 3' ends by regions respectively referred to as regions A and C, each of regions A and C comprising or consisting of nucleoside analogues, such as affinity-enhancing nucleoside analogues, such as 1-6 nucleoside analogues.

Typically, the gapmer comprises regions, from 5' to 3', A-B-C, or optionally A-B-C-D or D-A-B-C, wherein: region A consists of or comprises at least one nucleoside analogue, such as at least one LNA monomer, such as 1-6 nucleoside analogues, such as LNA monomers, and region B consists of or comprises at least five contiguous monomers which are capable of recruiting RNAse (when formed in a duplex with a complementary target region of the target RNA molecule, such as the mRNA target), such as DNA monomers; region C consists of or comprises at least one nucleoside analogue, such as at least one LNA monomer, such as 1-6 nucleoside analogues, such as LNA monomers; and region D, when present, consists of or comprises 1, 2 or 3 monomers, such as DNA monomers.

In various embodiments, region A consists of 1, 2, 3, 4, 5 or 6 nucleoside analogues, such as LNA monomers, such as 2-5 nucleoside analogues, such as 2-5 LNA monomers, such as 3 or 4 nucleoside analogues, such as 3 or 4 LNA monomers; and/or region C consists of 1, 2, 3, 4, 5 or 6 nucleoside analogues, such as LNA monomers, such as 2-5 nucleoside analogues, such as 2-5 LNA monomers, such as 3 or 4 nucleoside analogues, such as 3 or 4 LNA monomers.

In certain embodiments, region B consists of or comprises 5, 6, 7, 8, 9, 10, 11 or 12 contiguous monomers which are capable of recruiting RNAse, or 6-10, or 7-9, such as 8 contiguous monomers which are capable of recruiting RNAse. In certain embodiments, region B consists of or comprises at least one DNA monomer, such as 1-12 DNA monomers, preferably 4-12 DNA monomers, more preferably 6-10 DNA monomers, such as 7-10 DNA monomers, most preferably 8, 9 or 10 DNA monomers.

In various embodiments, region A consists of 3 or 4 nucleoside analogues, such as LNA monomers, region B consists of 7, 8, 9 or 10 DNA monomers, and region C consists of 3 or 4 nucleoside analogues, such as LNA monomers. Such designs include (A-B-C) 3-10-3, 3-10-4, 4-10-3, 3-9-3, 3-9-4, 4-9-3, 3-8-3, 3-8-4, 4-8-3, 3-7-3, 3-7-4, 4-7- 3, and may further include region D, which may have one or 2 monomers, such as DNA monomers. In a particular embodiment, the design includes (A-B-C) 3-10-3.

Further gapmer designs are disclosed in WO2004/046160, which is hereby incorporated by reference.

U.S. provisional application 60/977,409, hereby incorporated by reference, refers to 'shortmer' gapmer oligomers. In some embodiments, oligomers presented here may be such shortmer gapmers.

In certain embodiments, the oligomer consists of 10, 11, 12, 13 or 14 contiguous monomers, wherein the regions of the oligomer have the pattern (5'-3'), A-B-C, or optionally A-B-C-D or D-A-B-C, wherein: region A consists of 1, 2 or 3 nucleoside analogue monomers, such as LNA monomers; region B consists of 7, 8 or 9 contiguous monomers which are capable of recruiting RNAse when formed in a duplex with a complementary RNA molecule (such as a mRNA target); and region C consists of 1, 2 or 3 nucleoside analogue monomers, such as LNA monomers. When present, region D consists of a single DNA monomer.

In certain embodiments, region A consists of 1 LNA monomer. In certain embodiments, region A consists of 2 LNA monomers. In certain embodiments, region A consists of 3 LNA monomers. In certain embodiments, region C consists of 1 LNA monomer. In certain embodiments, region C consists of 2 LNA monomers. In certain embodiments, region C consists of 3 LNA monomers. In certain embodiments, region B consists of 7 nucleoside monomers. In certain embodiments, region B consists of 8 nucleoside monomers. In certain embodiments, region B consists of 9 nucleoside monomers. In certain embodiments, region B comprises 1-9 DNA monomers, such as 2, 3, 4, 5, 6, 7 or 8 DNA monomers. In certain embodiments, region B consists of DNA monomers. In certain embodiments, the number of monomers present in the A-B-C regions are selected from the group consisting of (nucleoside analogue monomers-region B-nucleoside analogue monomers): 1-8-1, 1-8-2, 2-8-1, 2-8-2, 3-8-3, 2-8-3, 3-8-2, 4-8-1, 4-8-2, 1-8-4, 2-8-4, or; 1-9-1, 1-9-2, 2-9-1, 2-9-2, 2-9-3, 3-9-2, 1-9-3, 3-9-1, 4-9-1, 1-9-4, or; 1-10-1, 1-10-2, 2-10-1, 2-10-2, 1-10-3, 3-10-1. In certain embodiments, the number of monomers present in the A-B-C regions of the oligomer of the disclosure is selected from the group consisting of: 2-7-1, 1-7-2, 2-7-2, 3-7-3, 2-7-3, 3-7-2, 3-7-4, and 4-7-3. In certain embodiments, each of regions A and C consists of two LNA monomers, and region B consists of 8 or 9 nucleoside monomers, preferably DNA monomers.

In various embodiments, other gapmer designs include those where regions A and/or C consists of 3, 4, 5 or 6 nucleoside analogues, such as monomers containing a 2'-O-methoxyethyl-ribose sugar (2'-MOE) or monomers containing a 2'-fluoro-deoxyribose sugar, and region B consists of 8, 9, 10, 11 or 12 nucleosides, such as DNA monomers, where regions A-B-C have 5-10-5 or 4-12-4 monomers. Further gapmer designs are disclosed in WO 2007/146511A2, hereby incorporated by reference.

3. Internucleoside Linkages

The monomers of the oligomers described herein are coupled together via linkage groups. Suitably, each monomer is linked to the 3' adjacent monomer via a linkage group.

The terms 'linkage group" or "internucleoside linkage" means a group capable of covalently coupling together two contiguous monomers. Specific and preferred examples include phosphate groups (forming a phosphodiester between adjacent nucleoside monomers) and phosphorothioate groups (forming a phosphorothioate linkage between adjacent nucleoside monomers).

Suitable linkage groups include those listed in PCT/DK2006/000512, for example in the first paragraph of page 34 of PCT/DK2006/000512 (hereby incorporated by reference). Other suitable linkage groups include those listed in U.S. Patent Publication No. 2006/0128646, which is hereby incorporated by reference. In various embodiments, the suitable linkage groups are selected from the group consisting of —O—P(O)$_2$—O—, —O—P(O,S)—O—, —O—P(S)$_2$—O—, —NR$^H$—P(O)$_2$—O—, —O—P(O,NR$^H$)—O—, —O—PO(R")—O—, —O—PO(CH$_3$)—O—, and —O—PO(NHR$^N$)—O—, where R$^H$ is selected form hydrogen and C$_{1-6}$-alkyl, and R" is selected from C$_{1-6}$-alkyl and phenyl.

In various embodiments, the linkage group is modified from its normal phosphodiester to one that is more resistant to nuclease attack, such as phosphorothioate or boranophosphate—these two being cleavable by RNase H, thereby permitting RNase-mediated antisense inhibition of expression of the target gene.

In some embodiments, suitable sulphur (S) containing linkage groups as provided herein are preferred. In various embodiments, phosphorothioate linkage groups are preferred, particularly for the gap region (B) of gapmers. In certain embodiments, phosphorothioate linkages are used to link together monomers in the flanking regions (A and C). In various embodiments, phosphorothioate linkages are used for linking regions A or C to region D, and for linking together monomers within region D.

In various embodiments, regions A, B and C, comprise linkage groups other than phosphorothioate, such as phosphodiester linkages, particularly, for instance when the use of nucleoside analogues protects the linkage groups within regions A and C from endo-nuclease degradation—such as when regions A and C comprise LNA monomers.

In various embodiments, adjacent monomers of the oligomer are linked to each other by means of phosphorothioate groups.

In certain embodiments, the inclusion of phosphodiester linkages, such as one or two linkages, into an oligomer with a phosphorothioate backbone, particularly with phosphorothioate linkage groups between or adjacent to nucleoside analogue monomers (typically in region A and/or C), modifies the bioavailability and/or bio-distribution of an oligomer—see WO2008/053314, hereby incorporated by reference.

In some embodiments, such as the embodiments referred to above, where suitable and not specifically indicated, all remaining linkage groups are either phosphodiester or phosphorothioate, or a mixture thereof.

In some embodiments all the internucleoside linkage groups are phosphorothioate.

When referring to specific gapmer oligonucleotide sequences, such as those provided herein, it will be understood that, in various embodiments, when the linkages are phosphorothioate linkages, alternative linkages, such as those disclosed herein may be used, for example phosphate (phosphodiester) linkages may be used, particularly for linkages between nucleoside analogues, such as LNA monomers. Likewise, in various embodiments, when referring to specific gapmer oligonucleotide sequences, such as those provided herein, when one or more monomers in region C comprises a 5-methylcytosine base, other monomers in that region may contain unmodified cytosine bases.

4. Target Nucleic Acid

The terms "nucleic acid" and "polynucleotide" are used interchangeably herein, and are defined as a molecule formed by covalent linkage of two or more monomers, as described above. Including two or more monomers, "nucleic acids" may be of any length, and the term is generic to "oligomers", which have the lengths described herein. The terms "nucleic acid" and "polynucleotide" include single-stranded, double-stranded, partially double-stranded, and circular molecules.

The term "target nucleic acid", as used herein, refers to DNA or RNA (e.g., mRNA or pre-mRNA) encoding a mammalian Myc polypeptide, such as human c-Myc, such as the nucleic acid having the sequence shown in SEQ ID NO: 1, and naturally occurring allelic variants of such nucleic acids. In certain embodiments, the mammalian Myc is a mouse Myc. In other embodiments, the mammalian Myc is a monkey Myc or a chimpanzee Myc. In some embodiments, for example when used in research or diagnostics, the "target nucleic acid" is a cDNA or a synthetic oligonucleotide derived from the above DNA or RNA nucleic acid targets. The oligomers according to the disclosure are typically capable of hybridizing to the target nucleic acid.

Exemplary target nucleic acids include mammalian Myc-encoding nucleic acids having the GenBank Accession numbers shown in Table 1 below, along with their corresponding protein sequences.

TABLE 1

|  | GenBank Accession Number Nucleic acid (mRNA/cDNA sequence) | GenBank Accession Number Polypeptide (deduced) |
|---|---|---|
| Human c-Myc | NM_002467.4 | NP_002458.2 |
| Human N-Myc | NM_005378.4 | NP_005369.2 |
| Mouse c-Myc | NM_010849 | NP_034979 |
|  | NM_001177353 | NP_001170824.1 |
| Mouse N-Myc | NM_008709.3 | NP_032735.3 |
| Rhesus monkey c-Myc | NM_001142873 | NP_001136345.1 |
| Chimpanzee | NM_001142794 | NP_001136266.1 |

The above-disclosed GenBank Accession numbers for nucleic acids refer to cDNA sequences and not to mRNA sequences per se. The sequence of a mature mRNA can be derived directly from the corresponding cDNA sequence with thymine bases (T) being replaced by uracil bases (U).

The term "naturally occurring variant thereof" refers to variants of a Myc polypeptide or nucleic acid sequence which exist naturally within the defined taxonomic group, such as mammalian, such as mouse, monkey, and preferably human Myc. Typically, when referring to "naturally occurring variants" of a polynucleotide the term also encompasses any allelic variant of Myc encoding genomic DNA which is found, for example, at the Chromosome 8:128.75-128.75 Mb (c-Myc) or at Chromosome 2: 16.08-16.09 Mb (N-Myc) by chromosomal translocation, duplication or rearrangement, or gene overexpression or amplification, and the RNA, such as mRNA derived therefrom. "Naturally occurring variants" may also include variants derived from alternative splicing of the Myc mRNA. When referenced to a specific polypeptide sequence, e.g., the term also includes naturally occurring forms of the protein which may therefore be processed, e.g. by co- or post-translational modifications, such as signal peptide cleavage, proteolytic cleavage, glycosylation, etc.

In certain embodiments, oligomers described herein bind to a region of the target nucleic acid (the "target region") by either Watson-Crick base pairing, Hoogsteen hydrogen bonding, or reversed Hoogsteen hydrogen bonding, between the monomers of the oligomer and monomers of the target nucleic acid. Such binding is also referred to as "hybridization." Unless otherwise indicated, binding is by Watson-Crick pairing of complementary bases (i.e., adenine with thymine (DNA) or uracil (RNA), and guanine with cytosine), and the oligomer binds to the target region because the sequence of the oligomer is identical to, or partially-identical to, the sequence of the reverse complement of the target region; for purposes herein, the oligomer is said to be "complementary" or "partially complementary" to the target region, and the percentage of "complementarity" of the oligomer sequence to that of the target region is the percentage "identity" to the reverse complement of the sequence of the target region.

Unless otherwise made clear by context, the "target region" herein will be the region of the target nucleic acid having the sequence that best aligns with the reverse complement of the sequence of the specified oligomer (or region thereof), using the alignment program and parameters described herein below.

In determining the degree of "complementarity" between oligomers of the disclosure (or regions thereof) and the target region of the nucleic acid which encodes mammalian Myc, such as those disclosed herein, the degree of "complementarity" (also, "homology") is expressed as the percentage identity between the sequence of the oligomer (or region thereof) and the reverse complement of the sequence of the target region that best aligns therewith. The percentage is calculated by counting the number of aligned bases that are identical as between the 2 sequences, dividing by the total number of contiguous monomers in the oligomer, and multiplying by 100. In such a comparison, if gaps exist, it is preferable that such gaps are merely mismatches rather than areas where the number of monomers within the gap differs between the oligomer and the target region.

Amino acid and polynucleotide alignments, percentage sequence identity, and degree of complementarity may be determined for purposes of the disclosure using the ClustalW algorithm using standard settings: Method: EMBOSS:: water (local): Gap Open=10.0, Gap extend=0.5, using Blosum 62 (protein), or DNAfull for nucleotide/nucleobase sequences.

Depending on context, "mismatch" refers to a non-identity in sequence (as, for example, between the nucleobase sequence of an oligomer and the reverse complement of the target region to which it binds; as for example, between the base sequence of two aligned Myc encoding nucleic acids), or to noncomplementarity in sequence (as, for example, between an oligomer and the target region to which it binds).

The oligomers which target Myc mRNA may hybridize to any site along the target mRNA nucleic acid, such as the 5' untranslated leader, exons, introns and 3' untranslated tail. However, it is preferred that the oligomers which target Myc mRNA hybridize to the mature mRNA form of the target nucleic acid in the coding region.

Suitably, the oligomer of the disclosure or conjugate thereof is capable of down-regulating expression of the Myc genes. In various embodiments, the oligomer (or conjugate) of the disclosure can effect the inhibition of Myc, typically in a mammalian cell, such as a human cell. In certain embodiments, the oligomers of the disclosure, or conjugates thereof, bind to the target nucleic acid and effect inhibition of Myc mRNA expression of at least 10% or 20% compared to the expression level immediately prior to dosing of the oligomer, more preferably of at least 30%, 40%, 50%, 60%, 70%, 80%, 90% or 95% as compared to the Myc expression level immediately prior to dosing of the oligomer. In some embodiments, such inhibition is seen when using from about 0.01 nM to about 50 nM of the oligomer or conjugate.

In various embodiments, the inhibition of mRNA expression is less than 100% (i.e., less than complete inhibition of expression), such as less than 98% inhibition, less than 95% inhibition, less than 90% inhibition, less than 80% inhibition, such as less than 70% inhibition. In various embodiments, modulation of gene expression can be determined by measuring protein levels, e.g. by the methods such as SDS-PAGE followed by western blotting using suitable antibodies raised against the target protein. Alternatively, modulation of expression levels can be determined by measuring levels of mRNA, e.g. by northern blotting or quantitative RT-PCR (qRT-PCR). When measuring via mRNA levels, the level of down-regulation when using an appropriate dosage, such as from about 0.04 nM to about 25 nM, such as from about 0.8 nM to about 20 nM, is, in various embodiments, typically to a level of 10-20% of the normal levels in the absence of the compound or conjugate of the disclosure.

In various embodiments, the disclosure provides oligomers, or a first region thereof, having a base sequence that is complementary to the sequence of a target region in a c-Myc nucleic acid, which oligomers down-regulate c-Myc mRNA and/or c-Myc protein expression and down-regulate the expression of mRNA and/or protein of one or more other Myc family members, such as N-Myc. Oligomers, or a first region thereof, that effectively bind to the target regions of two different Myc family nucleic acids (e.g., c-Myc and N-Myc mRNA) and that down-regulating the mRNA and/or protein expression of both targets are termed "bispecific." As used herein, the term "bispecific" is understood not to be limiting in any way. For example, a "bispecific oligomer" may have some effect on a third target nucleic acid.

In various embodiments, bispecific oligomers, or a first region thereof, are capable of binding to a target region in a c-Myc nucleic acid and a target region in an N-Myc target nucleic acid and effectively down-regulating the expression of c-Myc and N-Myc mRNA and/or protein. In certain embodiments, the bispecific oligomers do not down-regulate expression of c-Myc mRNA and/or protein and N-Myc mRNA and/or protein to the same extent.

In various embodiments, the disclosure therefore provides a method of inhibiting (e.g., by down-regulating) the expression of c-Myc protein and/or mRNA in a cell which is expressing c-Myc protein and/or mRNA, the method comprising contacting the cell with an amount of an oligomer or conjugate according to the disclosure effective to inhibit (e.g., to down-regulate) the expression of c-Myc protein and/or mRNA in said cell. Suitably the cell is a mammalian cell, such as a human cell. The contacting may occur, in certain embodiments, in vitro. In other embodiments, the contacting may be effected in vivo, by administering the compound or conjugate to a mammal. In various embodiments, the disclosure provides a method of inhibiting (e.g., by down-regulating) the expression of c-Myc protein and/or mRNA and the expression of N-Myc protein and/or mRNA in a cell.

5. Oligomer Sequences

In some embodiments, the oligomers of the disclosure have sequences that are identical to a sequence selected from the group consisting of SEQ ID NOs: 3-25.

Further provided are target nucleic acids (e.g., DNA or mRNA encoding, e.g., c-Myc or N-Myc) that contain target regions that are complementary or partially-complementary to one or more of the oligomers of the disclosure. In certain embodiments, the oligomers bind to variants of Myc target regions, such as allelic variants. In some embodiments, a variant of a Myc target region has at least 60%, more preferably at least 70%, more preferably at least 80%, more preferably at least 85%, more preferably at least 90%, more preferably at least 91%, at least 92%, at least 93%, at least 94%, at least 95% sequence identity to the target region in wild-type Myc. Thus, in other embodiments, the oligomers of the disclosure have sequences that differ in 1, 2 or 3 bases when compared to a sequence selected from the group consisting of SEQ ID NOs: 3-25. Typically, an oligomer of the disclosure that binds to a variant of a Myc target region is capable of inhibiting (e.g., by down-regulating) Myc.

In other embodiments, the oligomers are LNA oligomers, for example, those oligomers having the sequences shown in SEQ ID NOs: 26-48. In various embodiments, the oligomers are potent inhibitors of Myc mRNA and protein expression.

In various embodiments, the oligomer comprises or consists of a region having a base sequence which is identical or partially identical to the sequence of the reverse complement of a target region in SEQ ID NO: 1. In other embodiments, the oligomer comprises or consists of a region having a base sequence which is identical or partially identical to the sequence of the reverse complement of a target region in SEQ ID NO: 2.

In certain embodiments, the oligomer comprises or consists of a region having a base sequence which is fully complementary (perfectly complementary) to a target region of a nucleic acid which encodes a mammalian Myc protein.

However, in some embodiments, the oligomer includes 1, 2, 3, or 4 (or more) mismatches as compared to the best-aligned target region of a Myc target nucleic acid, and still sufficiently binds to the target region to effect inhibition of Myc mRNA or protein expression. The destabilizing effect of mismatches on Watson-Crick hydrogen-bonded duplex may, for example, be compensated by increased length of the oligomer and/or an increased number of nucleoside analogues, such as LNA monomers, present within the oligomer.

In various embodiments, the oligomer base sequence comprises no more than 3, such as no more than 2 mismatches compared to the base sequence of the best-aligned target region of, for example, a target nucleic acid which encodes a mammalian Myc protein.

In some embodiments, the oligomer base sequence comprises no more than a single mismatch when compared to the base sequence of the best-aligned target region of a nucleic acid which encodes a mammalian Myc protein.

In various embodiments, the base sequence of the oligomer, or of a first region thereof, is preferably at least 80% identical to a base sequence selected from the group consisting of SEQ ID NOs: 3-25, such as at least 85%, at least 90%, at least 91%, at least 92%, at least 93%, at least 94%, at least 95%, at least 96% identical, such as 100% identical.

In certain embodiments, the base sequence of the oligomer, or of a first region thereof, is at least 80% identical to the base sequence of the reverse complement of a target region present in SEQ ID NO: 1 or in SEQ ID NO: 2, such as at least 85%, at least 90%, at least 91%, at least 92% at least 93%, at least 94%, at least 95%, at least 96% identical, at least 97% identical, at least 98% identical, at least 99% identical, such as 100% identical.

In various embodiments, the base sequence of the oligomer, or of a first region thereof, is preferably at least 80% complementary to a target region of SEQ ID NO: 1, or of SEQ ID NO: 2, such as at least 85%, at least 90%, at least 91%, at least 92%, at least 93%, at least 94%, at least 95%, at least 96% complementary, at least 97% complementary, at least 98% complementary, at least 99% complementary, such as 100% complementary (perfectly complementary).

In some embodiments the oligomer, or a first region thereof, has a base sequence selected from the group consisting of SEQ ID NOs: 3, 4, 5, 6, 7, 8, 9, 10, 11, 12, 13, 14, 15, 16, 17, 18, 19, 20, 21, 22, 23, 24, and 25, or is selected from the group consisting of at least 10 contiguous monomers of SEQ ID NOs: 3, 4, 5, 6, 7, 8, 9, 10, 11, 12, 13, 14, 15, 16, 17, 18, 19, 20, 21, 22, 23, 24, and 25. In other embodiments, the sequence of the oligomer, or of a first region thereof, comprises one, two, or three base moieties that differ from those in oligomers having sequences of SEQ ID NOs: 3, 4, 5, 6, 7, 8, 9, 10, 11, 12, 13, 14, 15, 16, 17, 18, 19, 20, 21, 22, 23, 24, and 25, or the sequences of at least 10 contiguous monomers thereof, when optimally aligned with the selected sequence or region thereof.

In various embodiments, the oligomers comprise a region of 12, 13, 14, 15 or 16 contiguous monomers having a base sequence identically present in a sequence selected from the group consisting of SEQ ID NOs: 3, 4, 5, 6, 7, 8, 9, 10, 11, 12, 13, 14, 15, 16, 17, 18, 19, 20, 21, 22, 23, 24, and 25. In other embodiments, the oligomers include a region which comprises one, two, or three base moieties that differ from those in oligomers having sequences of SEQ ID NOs: 3, 4, 5, 6, 7, 8, 9, 10, 11, 12, 13, 14, 15, 16, 17, 18, 19, 20, 21, 22, 23, 24, and 25.

In some embodiments the region consists of 11, 12, 13, 14, 15, 16, 17, 18, 19, 20, 21, 22, 23, 24, 25, 26, 27, 28, or 29 contiguous monomers, such as 12-22, such as 12-18 monomers. Suitably, in some embodiments, the region is of the same length as the oligomer.

In some embodiments the oligomer comprises additional monomers at the 5' or 3' ends, such as, independently, 1, 2, 3, 4 or 5 additional monomers at the 5' end and/or the 3' end of the oligomer, which are non-complementary to the target region. In various embodiments, the oligomer comprises a region that is complementary to the target, which is flanked 5' and/or 3' by additional monomers. In some embodiments the additional 5' or 3' monomers are nucleosides, such as DNA or RNA monomers. In various embodiments, the 5' or 3' monomers represent region D as referred to in the context of gapmer oligomers described herein.

In certain embodiments, the oligomer consists of or comprises contiguous monomers having a nucleobase sequence according to SEQ ID NO: 26, or according to a region of at least 10 contiguous monomers thereof, such as 11, 12, 13, 14, 15 or 16 contiguous monomers thereof.

In certain embodiments, the oligomer consists of or comprises contiguous monomers having a nucleobase sequence according to SEQ ID NO: 27, or according to a region of at least 10 contiguous monomers thereof, such as 11, 12, 13, 14, 15 or 16 contiguous monomers thereof.

In certain embodiments, the oligomer consists of or comprises contiguous monomers having a nucleobase sequence according to SEQ ID NO: 28, or according to a region of at least 10 contiguous monomers thereof, such as 11, 12, 13, 14, 15 or 16 contiguous monomers thereof.

In certain embodiments, the oligomer consists of or comprises contiguous monomers having a nucleobase sequence according to SEQ ID NO: 29, or according to a region of at least 10 contiguous monomers thereof, such as 11, 12, 13, 14, 15 or 16 contiguous monomers thereof.

In certain embodiments, the oligomer consists of or comprises contiguous monomers having a nucleobase sequence according to SEQ ID NO: 30, or according to a region of at least 10 contiguous monomers thereof, such as 11, 12, 13, 14, 15 or 16 contiguous monomers thereof.

In certain embodiments, the oligomer consists of or comprises contiguous monomers having a nucleobase sequence according to SEQ ID NO: 31, or according to a region of at least 10 contiguous monomers thereof, such as 11, 12, 13, 14, 15 or 16 contiguous monomers thereof.

In certain embodiments, the oligomer consists of or comprises contiguous monomers having a nucleobase sequence according to SEQ ID NO: 32, or according to a region of at least 10 contiguous monomers thereof, such as 11, 12, 13, 14, 15 or 16 contiguous monomers thereof.

In certain embodiments, the oligomer consists of or comprises contiguous monomers having a nucleobase sequence according to SEQ ID NO: 33, or according to a region of at least 10 contiguous monomers thereof, such as 11, 12, 13, 14, 15 or 16 contiguous monomers thereof.

In certain embodiments, the oligomer consists of or comprises contiguous monomers having a nucleobase sequence according to SEQ ID NO: 34, or according to a region of at least 10 contiguous monomers thereof, such as 11, 12, 13, 14, 15 or 16 contiguous monomers thereof.

In certain embodiments, the oligomer consists of or comprises contiguous monomers having a nucleobase sequence according to SEQ ID NO: 35, or according to a region of at least 10 contiguous monomers thereof, such as 11, 12, 13, 14, 15 or 16 contiguous monomers thereof.

In certain embodiments, the oligomer consists of or comprises contiguous monomers having a nucleobase sequence according to SEQ ID NO: 36, or according to a region of at least 10 contiguous monomers thereof, such as 11, 12, 13, 14, 15 or 16 contiguous monomers thereof.

In certain embodiments, the oligomer consists of or comprises contiguous monomers having a nucleobase sequence according to SEQ ID NO: 37, or according to a region of at least 10 contiguous monomers thereof, such as 11, 12, 13, 14, 15 or 16 contiguous monomers thereof.

In certain embodiments, the oligomer consists of or comprises contiguous monomers having a nucleobase sequence according to SEQ ID NO: 38, or according to a region of at least 10 contiguous monomers thereof, such as 11, 12, 13, 14, 15 or 16 contiguous monomers thereof.

In certain embodiments, the oligomer consists of or comprises contiguous monomers having a nucleobase sequence according to SEQ ID NO: 39, or according to a region of at least 10 contiguous monomers thereof, such as 11, 12, 13, 14, 15 or 16 contiguous monomers thereof.

In certain embodiments, the oligomer consists of or comprises contiguous monomers having a nucleobase sequence according to SEQ ID NO: 40, or according to a region of at least 10 contiguous monomers thereof, such as 11, 12, 13, 14, 15 or 16 contiguous monomers thereof.

In certain embodiments, the oligomer consists of or comprises contiguous monomers having a nucleobase sequence according to SEQ ID NO: 41, or according to a region of at least 10 contiguous monomers thereof, such as 11, 12, 13, 14, 15 or 16 contiguous monomers thereof.

In certain embodiments, the oligomer consists of or comprises contiguous monomers having a nucleobase sequence according to SEQ ID NO: 42, or according to a region of at least 10 contiguous monomers thereof, such as 11, 12, 13, 14, 15 or 16 contiguous monomers thereof.

In certain embodiments, the oligomer consists of or comprises contiguous monomers having a nucleobase sequence according to SEQ ID NO: 43, or according to a region of at least 10 contiguous monomers thereof, such as 11, 12, 13, 14, 15 or 16 contiguous monomers thereof.

In certain embodiments, the oligomer consists of or comprises contiguous monomers having a nucleobase sequence according to SEQ ID NO: 44, or according to a region of at least 10 contiguous monomers thereof, such as 11, 12, 13, 14, 15 or 16 contiguous monomers thereof.

In certain embodiments, the oligomer consists of or comprises contiguous monomers having a nucleobase sequence according to SEQ ID NO: 45, or according to a region of at least 10 contiguous monomers thereof, such as 11, 12, 13, 14, 15 or 16 contiguous monomers thereof.

In certain embodiments, the oligomer consists of or comprises contiguous monomers having a nucleobase sequence according to SEQ ID NO: 46, or according to a region of at least 10 contiguous monomers thereof, such as 11, 12, 13, 14, 15 or 16 contiguous monomers thereof.

In certain embodiments, the oligomer consists of or comprises contiguous monomers having a nucleobase sequence according to SEQ ID NO: 47, or according to a region of at least 10 contiguous monomers thereof, such as 11, 12, 13, 14, 15 or 16 contiguous monomers thereof.

In certain embodiments, the oligomer consists of or comprises contiguous monomers having a nucleobase sequence according to SEQ ID NO: 48, or according to a region of at least 10 contiguous monomers thereof, such as 11, 12, 13, 14, 15 or 16 contiguous monomers thereof.

6. Nucleosides and Nucleoside Analogues

In various embodiments, at least one of the monomers present in the oligomer is a nucleoside analogue that contains a modified base, such as a base selected from 5-methylcytosine, isocytosine, pseudoisocytosine, 5-bromouracil, 5-propynyluracil, 6-aminopurine, 2-aminopurine, inosine, diaminopurine, 2-chloro-6-aminopurine, xanthine and hypoxanthine.

In various embodiments, at least one of the monomers present in the oligomer is a nucleoside analogue that contains a modified sugar.

In some embodiments, the linkage between at least 2 contiguous monomers of the oligomer is other than a phosphodiester linkage.

In certain embodiments, the oligomer includes at least one monomer that has a modified base, at least one monomer (which may be the same monomer) that has a modified sugar, and at least one inter-monomer linkage that is non-naturally occurring.

Specific examples of nucleoside analogues are described by e.g. Freier & Altmann; *Nucl. Acid Res.*, 1997, 25, 4429-4443 and Uhlmann; *Curr. Opinion in Drug Development*, 2000, 3(2), 293-213, and in Scheme 1 (in which some nucleoside analogues are shown as nucleotides):

Scheme 1

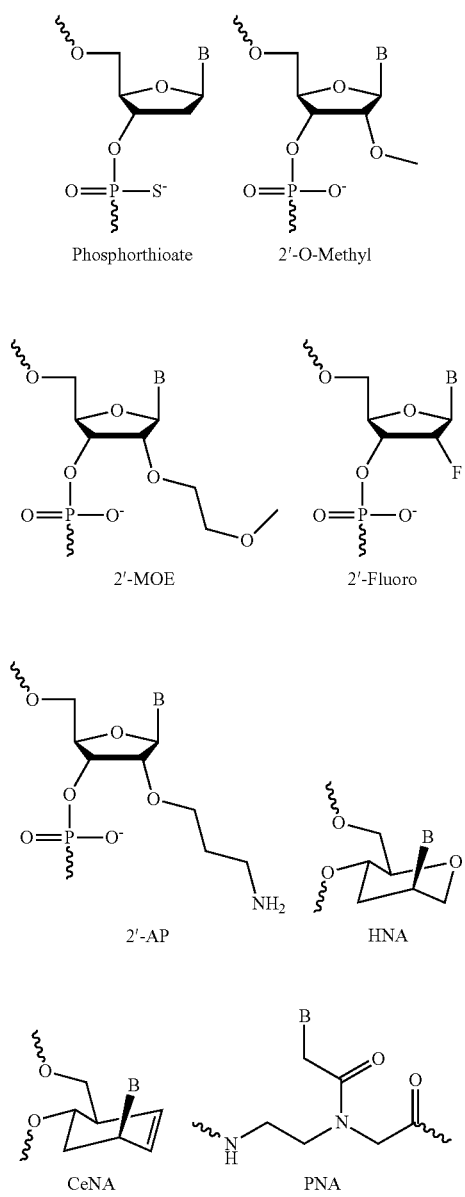

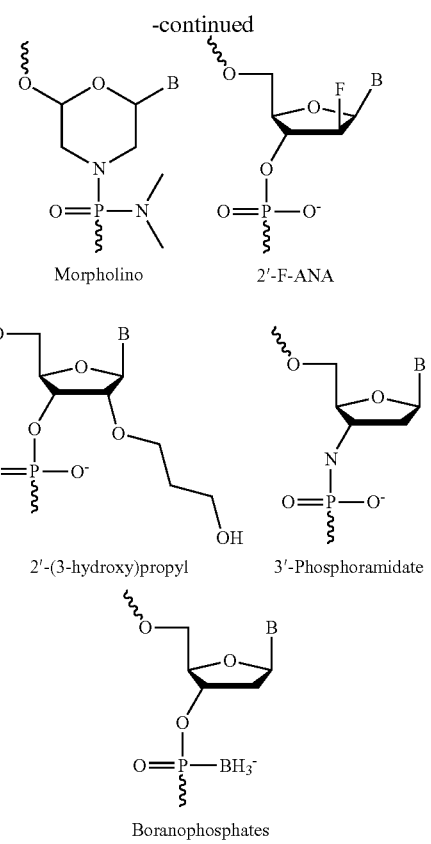

The oligomer may thus comprise or consist of a simple sequence of naturally occurring nucleosides—preferably DNA monomers, but also possibly RNA monomers, or a combination of nucleosides and one or more nucleoside analogues. In some embodiments, such nucleoside analogues suitably enhance the affinity of the oligomer for the target region of the target nucleic acid.

Examples of suitable and preferred nucleoside analogues are described in PCT/DK2006/000512, or are referenced therein.

In some embodiments, the nucleoside analogue comprises a sugar moiety modified to provide a 2'-substituent group, such as 2'-O-alkyl-ribose sugars, 2'-amino-deoxyribose sugars, and 2'-fluoro-deoxyribose sugars.

In some embodiments, the nucleoside analogue comprises a sugar in which a bridged structure, creating a bicyclic sugar (LNA), which enhances binding affinity and may also provide some increased nuclease resistance. In various embodiments, the LNA monomer is selected from oxy-LNA (such as beta-D-oxy-LNA, and alpha-L-oxy-LNA), and/or amino-LNA (such as beta-D-amino-LNA and alpha-L-amino-LNA) and/or thio-LNA (such as beta-D-thio-LNA and alpha-L-thio-LNA) and/or ENA (such as beta-D-ENA and alpha-L-ENA). In certain embodiments, the LNA monomers are beta-D-oxy-LNA. LNA monomers are further described below.

In various embodiments, incorporation of affinity-enhancing nucleoside analogues in the oligomer, such as LNA monomers or monomers containing 2'-substituted sugars, or incorporation of modified linkage groups provides increased nuclease resistance. In various embodiments, incorporation of affinity-enhancing nucleoside analogues allows the size of the oligomer to be reduced, and also reduces the size of the oligomer that binds specifically to a target region of a target sequence.

In some embodiments, the oligomer comprises at least 2 nucleoside analogues. In some embodiments, the oligomer comprises from 3-8 nucleoside analogues, e.g. 6 or 7 nucleoside analogues. In various embodiments, at least one of the nucleoside analogues is a locked nucleic acid (LNA) monomer; for example at least 3 or at least 4, or at least 5, or at least 6, or at least 7, or 8, nucleoside analogues are LNA monomers. In some embodiments, all the nucleoside analogues are LNA monomers.

It will be recognized that when referring to a preferred oligomer base sequence, in certain embodiments, the oligomers comprise a corresponding nucleoside analogue, such as a corresponding LNA monomer or other corresponding nucleoside analogue, which raise the duplex stability ($T_m$) of the oligomer/target region duplex (i.e. affinity enhancing nucleoside analogues).

In various embodiments, any mismatches (i.e., non-complementarities) between the base sequence of the oligomer and the base sequence of the target region, if present, are preferably located other than in the regions of the oligomer that contain affinity-enhancing nucleoside analogues (e.g., regions A or C), such as within region B as referred to herein, and/or within region D as referred to herein, and/or in regions consisting of DNA monomers, and/or in regions which are 5' or 3' to the region of the oligomer that is complementary to the target region.

In some embodiments the nucleoside analogues present within the oligomer (such as in regions A and C mentioned herein) are independently selected from, for example: monomers containing 2'-O-alkyl-ribose sugars, monomers containing 2'-amino-deoxyribose sugars, monomers containing 2'-fluoro-deoxyribose sugars, LNA monomers, monomers containing arabinose sugars ("ANA monomers"), monomers containing 2'-fluoro-arabinose sugars, monomers containing d-arabino-hexitol sugars ("HNA monomers"), intercalating monomers as defined in Christensen *Nucl. Acids. Res.*, 2002, 30: 4918-4925, hereby incorporated by reference, and 2'-O-methoxyethyl-ribose (2'MOE) sugars. In some embodiments, there is only one of the above types of nucleoside analogues present in the oligomer, or region thereof.

In certain embodiments, the nucleoside analogues contain 2'MOE sugars, 2'-fluoro-deoxyribose sugars, or LNA sugars, and as such the oligonucleotide of the disclosure may comprise nucleoside analogues which are independently selected from these three types. In certain oligomer embodiments containing nucleoside analogues, at least one of said nucleoside analogues contains a 2'-MOE-ribose sugar, such as 2, 3, 4, 5, 6, 7, 8, 9 or 10 nucleoside analogues containing 2'-MOE-ribose sugars. In some embodiments, at least one nucleoside analogue contains a 2'-fluoro-deoxyribose sugar, such as 2, 3, 4, 5, 6, 7, 8, 9 or 10 nucleoside analogues containing 2'-fluoro-DNA nucleotide sugars.

In various embodiments, the oligomer according to the disclosure comprises at least one Locked Nucleic Acid (LNA) monomer, such as 1, 2, 3, 4, 5, 6, 7, or 8 LNA monomers, such as 3-7 or 4 to 8 LNA monomers, or 3, 4, 5, 6 or 7 LNA monomers. In various embodiments, all the nucleoside analogues are LNA monomers. In certain embodiments, the oligomer comprises both beta-D-oxy-LNA monomers, and one or more of the following LNA monomers: thio-LNA monomers, amino-LNA monomers, oxy-LNA monomers, and/or ENA monomers in either the beta-D or alpha-L configurations, or combinations thereof. In certain embodiments, the cytosine base moieties of all LNA monomers in the oligomer are 5-methylcytosines. In certain embodiments, the oligomer comprises both LNA and DNA monomers. Typically, the combined total of LNA and DNA monomers is 10-25, preferably 10-20, even more preferably 12-16. In some embodiments, the oligomer or region thereof consists of at least one LNA monomer, and the remaining monomers are DNA monomers. In certain embodiments, the oligomer comprises only LNA monomers and nucleosides (such as RNA or DNA monomers, most preferably DNA monomers) optionally with modified linkage groups such as phosphorothioate.

In various embodiments, at least one of the nucleoside analogues present in the oligomer has a modified base selected from the group consisting of 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

7. LNA

The term "LNA monomer" refers to a nucleoside analogue containing a bicyclic sugar (an "LNA sugar"). The terms "LNA oligonucleotide" and "LNA oligomer" refer to an oligomer containing one or more LNA monomers.

The LNA used in the oligonucleotide compounds of the disclosure preferably has the structure of the general formula I:

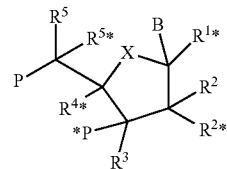

wherein X is selected from —O—, —S—, —N($R^{N*}$)—, —C($R^6R^{6*}$)—;

B is selected from hydrogen, optionally substituted $C_{1-4}$-alkoxy, optionally substituted $C_{1-4}$-alkyl, optionally substituted $C_{1-4}$-acyloxy, nucleobases, DNA intercalators, photochemically active groups, thermochemically active groups, chelating groups, reporter groups, and ligands;

P designates the radical position for an internucleoside linkage to a succeeding monomer, or a 5'-terminal group, such internucleoside linkage or 5'-terminal group optionally including the substituent $R^5$ or equally applicable the substituent $R^{5*}$;

P* designates an internucleoside linkage to a preceding monomer, or a 3'-terminal group; $R^{4*}$ and $R^{2*}$ together designate a biradical consisting of 1-4 groups/atoms selected from —C($R^aR^b$)—, —C($R^a$)=C($R^b$)—, —C($R^a$)=N—, —O—, —Si($R^a$)$_2$—, —S—, —SO$_2$—, —N($R^a$)—, and >C=Z, wherein Z is selected from —O—, —S—, and —N($R^a$)—, and $R^a$ and $R^b$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene ($=CH_2$), and each of the substituents $R^{1*}$, $R^2$, $R^3$, $R^5$, $R^{5*}$, $R^6$ and $R^{6*}$, which are present is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents together may designate oxo, thioxo, imino, or optionally substituted methylene, or together may form a spiro biradical consisting of a 1-5 carbon atom(s) alkylene chain which is optionally interrupted and/or terminated by one or more heteroatoms/groups selected from —O—, —S—, and —(NR$^N$)— where R$^N$ is selected from hydrogen and $C_{1-4}$-alkyl, and where two adjacent (non-geminal) substituents may designate an additional bond resulting in a double bond; and R$^{N*}$, when present and not involved in a biradical, is selected from hydrogen and $C_{1-4}$-alkyl; and basic salts and acid addition salts thereof.

In some embodiments, $R^{5*}$ is selected from H, —CH$_3$, —CH$_2$—CH$_3$, —CH$_2$—O—CH$_3$, and —CH=CH$_2$.

In various embodiments, $R^{4*}$ and $R^{2*}$ together designate a biradical selected from —C(R$^a$R$^b$)—O—, —C(R$^a$R$^b$)—C(R$^c$R$^d$)—O—, —C(R$^a$R$^b$)—C(R$^c$R$^d$)—C(R$^e$R$^f$)—O—, —C(R$^a$R$^b$)—O—C(R$^c$R$^d$)—, —C(R$^a$R$^b$)—O—C(R$^c$R$^d$)—O—, —C(R$^a$R$^b$)—C(R$^c$R$^d$)—, —C(R$^a$R$^b$)—C(R$^c$R$^d$)—C(R$^e$R$^f$)—, —C(R$^a$)=C(R$^b$)—C(R$^c$R$^d$)—, —C(R$^a$R$^b$)—N(R$^c$)—, —C(R$^a$R$^b$)—C(R$^c$R$^d$)—N(R$^e$)—, —C(R$^a$R$^b$)—N(R$^c$)—O—, and —C(R$^a$R$^b$)—S—, —C(R$^a$R$^b$)—C(R$^c$R$^d$)—S—, wherein R$^a$, R$^b$, R$^c$, R$^d$, R$^e$, and R$^f$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene ($=CH_2$), In a further embodiment $R^{4*}$ and $R^{2*}$ together designate a biradical (bivalent group) selected from —CH$_2$—O—, —CH$_2$—S—, —CH$_2$—NH—, —CH$_2$—N(CH$_3$)—, —CH$_2$—CH$_2$—O—, —CH$_2$—CH(CH$_3$)—, —CH$_2$—CH$_2$—S—, —CH$_2$—CH$_2$—NH—, —CH$_2$—CH$_2$—CH$_2$—, —CH$_2$—CH$_2$—CH$_2$—O—, —CH$_2$—CH$_2$—CH(CH$_3$)—, —CH=CH—CH$_2$—, —CH$_2$—O—CH$_2$—O—, —CH$_2$—NH—O—, —CH$_2$—N(CH$_3$)—O—, —CH$_2$—O—CH$_2$—, —CH(CH$_3$)—O—, and —CH(CH$_2$—O—CH$_3$)—O—.

For all chiral centers, asymmetric groups may be found in either R or S orientation.

Preferably, the LNA monomer used in the oligomer of the disclosure comprises at least one LNA monomer according to any of the formulas

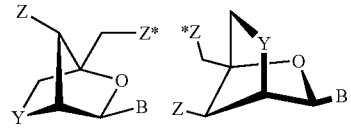

wherein Y is —O—, —O—CH2-, —S—, —NH—, or N(RH); Z and Z* are independently selected among an internucleotide linkage, a terminal group or a protecting group; B constitutes a natural or non-natural nucleotide base moiety, and $R^H$ is selected from hydrogen and $C_{1-4}$-alkyl.

Specifically preferred LNA monomers are shown in Scheme 2:

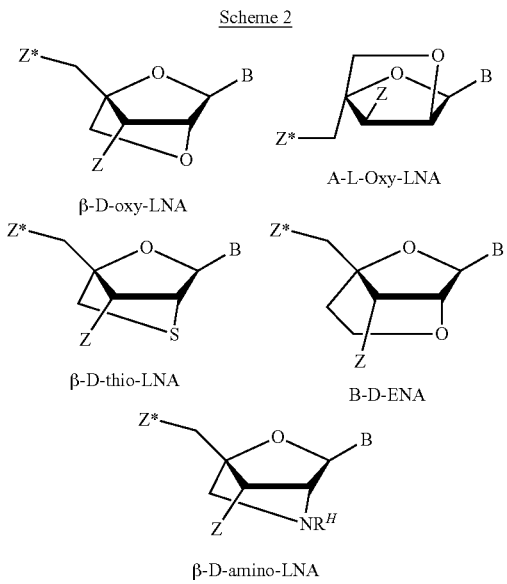

The term "thio-LNA" refers to an LNA monomer in which Y in the general formula above is selected from S or —CH$_2$—S—. Thio-LNA can be in either the beta-D or alpha-L-configuration.

The term "amino-LNA" refers to an LNA monomer in which Y in the general formula above is selected from —N(H)—, N(R)—, CH$_2$—N(H)—, and —CH$_2$—N(R)— where R is selected from hydrogen and $C_{1-4}$-alkyl. Amino-LNA can be in either the beta-D or alpha-L-configuration.

The term "oxy-LNA" refers to an LNA monomer in which Y in the general formula above represents —O— or —CH$_2$—O—. Oxy-LNA can be in either the beta-D or alpha-L-configuration.

The term "ENA" refers to an LNA monomer in which Y in the general formula above is —CH$_2$—O— (where the oxygen atom of —CH$_2$—O— is attached to the 2'-position relative to the base B).

In various embodiments, the LNA monomer is selected from a beta-D-oxy-LNA monomer, and alpha-L-oxy-LNA monomer, a beta-D-amino-LNA monomer, and beta-D-thio-LNA monomer, in particular a beta-D-oxy-LNA monomer.

In the present context, the term "$C_{1-4}$ alkyl" means a linear or branched saturated hydrocarbon chain wherein the chain has from one to four carbon atoms, such as methyl, ethyl, n-propyl, isopropyl, n-butyl, isobutyl, sec-butyl and tert-butyl.

8. RNAse H Recruitment

In some embodiments, an oligomer functions via non-RNase-mediated degradation of a target mRNA, such as by steric hindrance of translation, or other mechanisms; however, in various embodiments, oligomers of the disclosure are capable of recruiting an endo-ribonuclease (RNase), such as RNase H.

Typically, the oligomer comprises a region of at least 6, such as at least 7 contiguous monomers, such as at least 8 or at least 9 contiguous monomers, including 7, 8, 9, 10, 11, 12, 13, 14, 15 or 16 contiguous monomers, which, when forming a duplex with the target region of the target RNA, is capable of recruiting RNase. The region of the oligomer which is capable of recruiting RNAse may be region B, as referred to in the context of a gapmer as described herein. In some embodiments, the region of the oligomer which is capable of recruiting RNAse, such as region B, consists of 10, 11, 12, 13, 14, 15, 16, 17, 18, 19 or 20 monomers.

EP 1 222 309 provides in vitro methods for determining RNaseH activity, which may be used to determine the ability of the oligomers to recruit RNaseH. An oligomer is deemed capable of recruiting RNaseH if, when contacted with the complementary region of the RNA target, it has an initial rate, as measured in pmol/l/min, of at least 1%, such as at least 5%, such as at least 10% or less than 20% of an oligonucleotide having the same base sequence but containing only DNA monomers, with no 2' substitutions, with phosphorothioate linkage groups between all monomers in the oligonucleotide, using the methodology provided by Examples 91-95 of EP 1 222 309, incorporated herein by reference.

In some embodiments, an oligomer is deemed essentially incapable of recruiting RNaseH if, when contacted with the complementary target region of the RNA target, and RNaseH, the RNaseH initial rate, as measured in pmol/l/min, is less than 1%, such as less than 5%, such as less than 10% or less than 20% of the initial rate determined using an oligonucleotide having the same base sequence, but containing only DNA monomers, with no 2' substitutions, with phosphorothioate linkage groups between all monomers in the oligonucleotide, using the methodology provided by Examples 91-95 of EP 1 222 309.

In other embodiments, an oligomer is deemed capable of recruiting RNaseH if, when contacted with the complementary target region of the RNA target, and RNaseH, the RNaseH initial rate, as measured in pmol/l/min, is at least 20%, such as at least 40%, such as at least 60%, such as at least 80% of the initial rate determined using an oligonucleotide having the same base sequence, but containing only DNA monomers, with no 2' substitutions, with phosphorothioate linkage groups between all monomers in the oligonucleotide, using the methodology provided by Examples 91-95 of EP 1 222 309.

Typically, the region of the oligomer which forms the duplex with the complementary target region of the target RNA and is capable of recruiting RNase contains DNA monomers and LNA monomers and forms a DNA/RNA-like duplex with the target region.

In various embodiments, the oligomer comprises both nucleosides and nucleoside analogues, and is in the form of a gapmer, a headmer or a mixmer.

A "headmer" is defined as an oligomer that comprises a first region and a second region that is contiguous thereto, with the 5'-most monomer of the second region linked to the 3'-most monomer of the first region. The first region comprises a contiguous stretch of non-RNase recruiting nucleoside analogues and the second region comprises a contiguous stretch (such as at least 7 contiguous monomers) of DNA monomers or nucleoside analogue monomers recognizable and cleavable by the RNase.

A "tailmer" is defined as an oligomer that comprises a first region and a second region that is contiguous thereto, with the 5'-most monomer of the second region linked to the 3'-most monomer of the first region. The first region comprises a contiguous stretch (such as at least 7 contiguous monomers) of DNA monomers or nucleoside analogue monomers recognizable and cleavable by the RNase, and the second region comprises a contiguous stretch of non-RNase recruiting nucleoside analogues.

Other "chimeric" oligomers, called "mixmers", consist of an alternating composition of (i) DNA monomers or nucleoside analogue monomers recognizable and cleavable by RNase, and (ii) non-RNase recruiting nucleoside analogue monomers.

In some embodiments, in addition to enhancing affinity of the oligomer for the target region, some nucleoside analogues also mediate RNase (e.g., RNaseH) binding and cleavage. Since α-L-LNA monomers recruit RNaseH activity to a certain extent, in some embodiments, gap regions (e.g., region B as referred to herein) of oligomers containing α-L-LNA monomers consist of fewer monomers recognizable and cleavable by the RNaseH, and more flexibility in the mixmer construction is introduced.

9. Conjugates

In the context of this disclosure, the term "conjugate" indicates a compound formed by the covalent attachment ("conjugation") of an oligomer as described herein, to one or more moieties that are not themselves nucleic acids or monomers ("conjugated moieties"). Examples of such conjugated moieties include macromolecular compounds such as proteins, fatty acid chains, sugar residues, glycoproteins, polymers, or combinations thereof. Typically proteins may be antibodies for a target protein. Typical polymers may be polyethylene glycol. Conjugated moieties may possess biological activity, such as drugs including, but not limited to, small molecules.

Accordingly, provided herein are conjugates comprising an oligomer as herein described, and at least one conjugated moiety that is not a nucleic acid or monomer, covalently attached to said oligomer. Therefore, in certain embodiments where the oligomer consists of contiguous monomers having a specified sequence of bases, as herein disclosed, the conjugate may also comprise at least one conjugated moiety that is covalently attached to the oligomer.

In various embodiments, the oligomer is conjugated to a moiety that increases the cellular uptake of oligomeric compounds. WO2007/031091 provides suitable ligands and conjugates, which are hereby incorporated by reference.

In various embodiments, conjugation (to a conjugated moiety) may enhance the activity, cellular distribution or cellular uptake of the oligomer of the disclosure. Such moieties include, but are not limited to, antibodies, polypeptides, lipid moieties such as a cholesterol moiety, cholic acid, a thioether, e.g. Hexyl-s-tritylthiol, a thiocholesterol, an aliphatic chain, e.g., dodecandiol or undecyl residues, a phospholipids, e.g., di-hexadecyl-rac-glycerol or triethylammonium 1,2-di-o-hexadecyl-rac-glycero-3-h-phosphonate, a polyamine or a polyethylene glycol chain, an adamantane acetic acid, a palmityl moiety, an octadecylamine or hexylamino-carbonyl-oxycholesterol moiety.

In certain embodiments, the oligomers are conjugated to active drug substances, for example, aspirin, ibuprofen, a sulfa drug, an antidiabetic, an antibacterial or an antibiotic.

In certain embodiments the conjugated moiety is a sterol, such as cholesterol.

In various embodiments, the conjugated moiety comprises or consists of a positively charged polymer, such as a positively charged peptides of, for example 1-50, such as 2-20 such as 3-10 amino acid residues in length, and/or polyalkylene oxide such as polyethylene glycol (PEG) or polypropylene glycol—see WO 2008/034123, hereby incorporated by reference. Suitably the positively charged polymer, such as a polyalkylene oxide may be attached to the oligomer of the disclosure via a linker such as the releasable linker described in WO 2008/034123.

By way of example, the following moieties may be used in the conjugates of the disclosure:

biodegradable. See e.g., U.S. Pat. No. 7,087,229, which is incorporated by reference herein in its entirety.

In some embodiments, oligomers are functionalized at the 5' end in order to allow covalent attachment of the conjugated moiety to the 5' end of the oligomer. In other embodiments, oligomers can be functionalized at the 3' end. In still other embodiments, oligomers can be functionalized along the backbone or on the heterocyclic base moiety. In yet other embodiments, oligomers can be functionalized at more than one position independently selected from the 5' end, the 3' end, the backbone and the base.

In some embodiments, activated oligomers are synthesized by incorporating during the synthesis one or more monomers that is covalently attached to a functional moiety. In other embodiments, activated oligomers are synthesized with monomers that have not been functionalized, and the oligomer is functionalized upon completion of synthesis.

In some embodiments, the oligomers are functionalized with a hindered ester containing an aminoalkyl linker, wherein the alkyl portion has the formula $(CH_2)_w$, wherein w is an integer ranging from 1 to 10, preferably about 6, wherein the alkyl portion of the alkylamino group can be straight chain or branched chain, and wherein the functional group is attached to the oligomer via an ester group (—O—C(O)—$(CH_2)_w$NH).

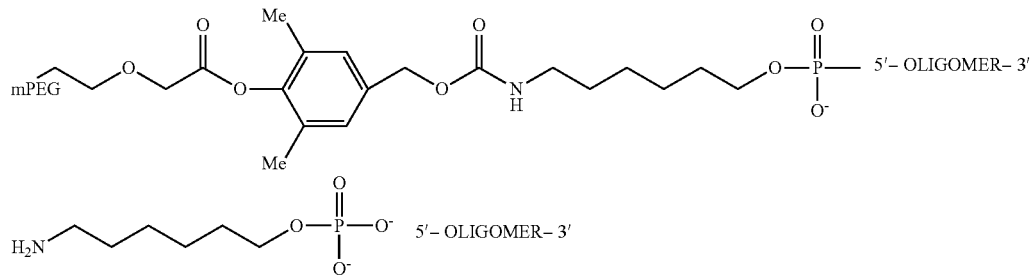

9.1. Activated Oligomers

The term "activated oligomer," as used herein, refers to an oligomer that is covalently linked (i.e., functionalized) to at least one functional moiety that permits covalent linkage of the oligomer to one or more conjugated moieties, i.e., moieties that are not themselves nucleic acids or monomers, to form the conjugates herein described. Typically, a functional moiety will comprise a chemical group that is capable of covalently bonding to the oligomer via, e.g., a 3'-hydroxyl group or the exocyclic $NH_2$ group of the adenine base, a spacer that is preferably hydrophilic and a terminal group that is capable of binding to a conjugated moiety (e.g., an amino, sulfhydryl or hydroxyl group). In some embodiments, this terminal group is not protected, e.g., is an $NH_2$ group. In other embodiments, the terminal group is protected, for example, by any suitable protecting group such as those described in "Protective Groups in Organic Synthesis" by Theodora W. Greene and Peter G. M. Wuts, 3rd edition (John Wiley & Sons, 1999). Examples of suitable hydroxyl protecting groups include esters such as acetate ester, aralkyl groups such as benzyl, diphenylmethyl, or triphenylmethyl, and tetrahydropyranyl. Examples of suitable amino protecting groups include benzyl, alpha-methylbenzyl, diphenylmethyl, triphenylmethyl, benzyloxycarbonyl, tert-butoxycarbonyl, and acyl groups such as trichloroacetyl or trifluoroacetyl.

In some embodiments, the functional moiety is self-cleaving. In other embodiments, the functional moiety is In other embodiments, the oligomers are functionalized with a hindered ester containing a $(CH_2)_w$-sulfhydryl (SH) linker, wherein w is an integer ranging from 1 to 10, preferably about 6, wherein the alkyl portion of the alkylamino group can be straight chain or branched chain, and wherein the functional group attached to the oligomer via an ester group (—O—C(O)—$(CH_2)_w$SH). In some embodiments, sulfhydryl-activated oligonucleotides are conjugated with polymer moieties such as polyethylene glycol or peptides (via formation of a disulfide bond).

Activated oligomers containing hindered esters as described above can be synthesized by any method known in the art, and in particular, by methods disclosed in PCT Publication No. WO 2008/034122 and the examples therein, which is incorporated herein by reference in its entirety.

Activated oligomers covalently linked to at least one functional moiety can be synthesized by any method known in the art, and in particular, by methods disclosed in U.S. Patent Publication No. 2004/0235773, which is incorporated herein by reference in its entirety, and in Zhao et al., *J. Controlled Release* 2007, 119:143-152; and Zhao et al. *Bioconjugate Chem.,* 2005, 16:758-766.

In still other embodiments, the oligomers are functionalized by introducing sulfhydryl, amino or hydroxyl groups into the oligomer by means of a functionalizing reagent substantially as described in U.S. Pat. Nos. 4,962,029 and 4,914,210, i.e., a substantially linear reagent having a phosphoramidite at one end linked through a hydrophilic spacer chain to the opposing end which comprises a protected or unprotected sulfhydryl, amino or hydroxyl group. Such reagents primarily react with hydroxyl groups of the oligomer. In some embodiments, such activated oligomers have a functionalizing reagent coupled to a 5'-hydroxyl group of the oligomer. In other embodiments, the activated oligomers have a functionalizing reagent coupled to a 3'-hydroxyl group. In still other embodiments, the activated oligomers have a functionalizing reagent coupled to a hydroxyl group on the backbone of the oligomer. In yet further embodiments, the oligomer is functionalized with more than one of the functionalizing reagents as described in U.S. Pat. Nos. 4,962,029 and 4,914,210, incorporated herein by reference in their entirety. Methods of synthesizing such functionalizing reagents and incorporating them into monomers or oligomers are disclosed in U.S. Pat. Nos. 4,962,029 and 4,914,210.

In some embodiments, the 5'-terminus of a solid-phase bound oligomer is functionalized with a dienyl phosphoramidite derivative, followed by conjugation of the deprotected oligomer with, e.g., an amino acid or peptide via a Diels-Alder cycloaddition reaction.

In various embodiments, the incorporation of monomers containing 2'-sugar modifications, such as a 2'-carbamate substituted sugar or a 2'-(O-pentyl-N-phthalimido)-deoxyribose sugar into the oligomer facilitates covalent attachment of conjugated moieties to the sugars of the oligomer. In other embodiments, an oligomer with an amino-containing linker at the 2'-position of one or more monomers is prepared using a reagent such as, for example, 5'-dimethoxytrityl-2'-O-(e-phthalimidylaminopentyl)-2'-deoxyadenosine-3'-N,N-diisopropyl-cyanoethoxy phosphoramidite. See, e.g., Manoharan, et al., *Tetrahedron Letters*, 1991, 34, 7171.

In still further embodiments, the oligomers have amine-containing functional moieties on the nucleobase, including on the N6 purine amino groups, on the exocyclic N2 of guanine, or on the N4 or 5 positions of cytosine. In various embodiments, such functionalization may be achieved by using a commercial reagent that is already functionalized in the oligomer synthesis.

Some functional moieties are commercially available, for example, heterobifunctional and homobifunctional linking moieties are available from the Pierce Co. (Rockford, Ill.). Other commercially available linking groups are 5'-Amino-Modifier C6 and 3'-Amino-Modifier reagents, both available from Glen Research Corporation (Sterling, Va.). 5'-Amino-Modifier C6 is also available from Life Technologies (Foster City, Calif.) as Aminolink-2, and 3'-Amino-Modifier is also available from Clontech Laboratories Inc. (Palo Alto, Calif.).

10. Compositions

In various embodiments, the oligomer of the disclosure is used in pharmaceutical formulations and compositions. Suitably, such compositions comprise a pharmaceutically acceptable diluent, carrier, salt or adjuvant. PCT/DK2006/000512 provides suitable and preferred pharmaceutically acceptable diluents, carriers and adjuvants—which are hereby incorporated by reference. Suitable dosages, formulations, administration routes, compositions, dosage forms, combinations with other therapeutic agents, pro-drug formulations are also provided in PCT/DK2006/000512—which are also hereby incorporated by reference. Details on techniques for formulation and administration also may be found in the latest edition of "REMINGTON'S PHARMACEUTICAL SCIENCES" (Maack Publishing Co, Easton Pa.).

In some embodiments, an oligomer of the disclosure is covalently linked to a conjugated moiety to aid in delivery of the oligomer across cell membranes. An example of a conjugated moiety that aids in delivery of the oligomer across cell membranes is a lipophilic moiety, such as cholesterol. In various embodiments, an oligomer of the disclosure is formulated with lipid formulations that form liposomes, such as Lipofectamine 2000 or Lipofectamine RNAiMAX, both of which are commercially available from Invitrogen. In some embodiments, the oligomers are formulated with a mixture of one or more lipid-like non-naturally occurring small molecules ("lipidoids"). Libraries of lipidoids can be synthesized by conventional synthetic chemistry methods and various amounts and combinations of lipidoids can be assayed in order to develop a vehicle for effective delivery of an oligomer of a particular size to the targeted tissue by the chosen route of administration. Suitable lipidoid libraries and compositions can be found, for example in Akinc et al., *Nature Biotechnol.*, 2008, 26, 561-569, which is incorporated by reference herein.

As used herein, the term "pharmaceutically acceptable salts" refers to salts that retain the desired biological activity of the herein identified compounds and exhibit acceptable levels of undesired toxic effects. Non-limiting examples of such salts can be formed with organic amino acid and base addition salts formed with metal cations such as zinc, calcium, bismuth, barium, magnesium, aluminum, copper, cobalt, nickel, cadmium, sodium, potassium, and the like, or with a cation formed from ammonia, N,N'-dibenzylethylene-diamine, D-glucosamine, tetraethylammonium, or ethylenediamine; or (c) combinations of (a) and (b); e.g., a zinc tannate salt or the like.

In certain embodiments, the pharmaceutical compositions comprise other active ingredients in addition to an oligomer or conjugate of the disclosure, including active agents useful for the treatment of cancer, such as hematological cancers, solid tumors, hepatocellular carcinoma, ovarian cancer and prostate cancer. In various embodiments, the pharmaceutical compositions comprise in addition to an oligomer or conjugate one or more compounds that inhibit agents acting upstream or downstream of Myc. In certain embodiments, such compounds include, but are not limited to, inhibitors of WNT, β-catenin, MAX, BRD-4, cyclin dependant kinases, miR-17-92, p53 and SUMOylation pathways.

The disclosure also provides a kit of parts wherein a first part comprises at least one oligomer, conjugate and/or the pharmaceutical composition according to the disclosure and a further part comprises an active agent useful for the treatment of cancer or an inhibitor of agents that interact with Myc. It is therefore envisaged that the kit of parts may be used in a method of treatment, as referred to herein, where the method comprises administering both the first part and the further part, either simultaneously or one after the other.

11. Uses

The term "treatment" as used herein refers to both treatment of an existing disease (e.g., a disease or disorder as referred to herein below), or prevention of a disease, i.e., prophylaxis. It will therefore be recognized that, in certain embodiments, "treatment" includes prophylaxis.

In various embodiments, the oligomers of the disclosure may be utilized as research reagents for, for example, diagnostics, therapeutics and prophylaxis.

In some embodiments, such oligomers may be used for research purposes to specifically inhibit the expression of Myc protein (typically by degrading or inhibiting the Myc mRNA and thereby preventing protein formation) in cells and experimental animals, thereby facilitating functional analysis of the target or an appraisal of its usefulness as a target for therapeutic intervention.

In certain embodiments, the oligomers may be used in diagnostics to detect and quantify Myc expression in cells and tissues by northern blotting, in-situ hybridization or similar techniques.

In various therapeutic embodiments, a non-human animal or a human suspected of having a disease or disorder which can be treated by modulating the expression of Myc is treated by administering an effective amount of an oligomer of the disclosure. Further provided are methods of treating a mammal, such as treating a human, suspected of having or being prone to a disease or condition, associated with expression of Myc by administering a therapeutically or prophylactically effective amount of one or more of the oligomers, conjugates or compositions described herein.

In certain embodiments, the disclosure also provides for the use of the compounds or conjugates described herein for the manufacture of a medicament for the treatment of a disorder as referred to herein, or for a method of the treatment of a disorder as referred to herein.

In various embodiments, the disclosure also provides for a method for treating a disorder as referred to herein, said method comprising administering a compound as herein described, and/or a conjugate thereof, and/or a pharmaceutical composition to a patient in need thereof.

11.1. Medical Indications

In certain therapeutic embodiments, the disorder to be treated is cancer, such as prostate cancer or breast cancer. In various embodiments, the treatment of such a disease or condition may be combined with one or more other anti-cancer treatments, such as radiotherapy, chemotherapy or immunotherapy.

In various embodiments, the disease or disorder is associated with a mutation of the Myc gene or a gene whose protein product is associated with or interacts with Myc. Therefore, in various embodiments, the target mRNA is a mutated form of the Myc sequence, for example, it comprises one or more single point mutations. In certain embodiments, the disease or disorder is associated with rearrangement and/or amplification of the Myc gene. In some embodiments, the disease or disorder is associated with translocation of the Myc gene. In other embodiments, the disease or disorder is associated with overexpression of the Myc gene.

In particular embodiments, the disease or disorder associated with mutation and/or rearrangement and/or amplification and/or overexpression and/or rearrangement of the Myc gene is selected from the group consisting of hematological cancers, including but not limited to B-acute lymphocytic leukemia, Burkitt's lymphoma, diffuse large cell lymphoma, multiple myeloma, and primary plasma cell leukemia; solid tumors, including but not limited to, atypical carcinoid lung cancer, bladder cancer, breast cancer, cervical cancer, colon cancer, gastric cancer, glioblastoma, hepatocellular carcinoma, large cell neuroendocrine carcinoma, medulloblastoma, melanoma, neuroblastoma, oesophageal squamous cell carcinoma, osteosarcoma, ovarian cancer, prostate cancer, renal clear cell carcinoma retinoblastoma, rhabdomyocarcoma and small cell lung carcinoma.

In certain embodiments, the cancer to be treated is resistant to traditional chemotherapies, e.g., alkylating agents such as cisplatinum, taxanes, vinca alkaloids such as vincristine and vinblastine, topoisomerase inhibitors such as etoposide, cytotoxic antibiotics, and endocrine therapies. In particular embodiments, the cancer to be treated is resistant to traditional chemotherapies due, at least in part, to overexpression of c-Myc.

In other embodiments, the disease or disorder is associated with abnormal levels of a mutated form of Myc protein.

The disclosure further provides use of a compound described herein in the manufacture of a medicament for the treatment of any and all conditions disclosed herein.

In various embodiments, the disclosure is directed to a method of treating a mammal suffering from or susceptible to a condition associated with abnormal levels of Myc mRNA or protein, comprising administering to the mammal a therapeutically effective amount of an oligomer, or a conjugate thereof, that comprises one or more LNA monomers.

In certain embodiments, the disclosure is directed to the use of an oligomer (compound) as described herein or a conjugate thereof for the preparation of a medicament for the treatment of a condition as disclosed herein above.

In various embodiments, the disclosure encompasses a method of preventing or treating a disease comprising administering a therapeutically effective amount of an oligomer as described herein, or a conjugate thereof, to a human in need of such therapy.

In certain embodiments, the LNA oligomers of the disclosure, or conjugates thereof, are administered for a short period time rather than continuously.

In certain embodiments, the oligomer (compound) is linked to a conjugated moiety, for example, in order to increase the cellular uptake of the oligomer. In one embodiment the conjugated moiety is a sterol, such as cholesterol, or a vitamin E or alpha-tocopherol.

In various embodiments, the disclosure is directed to a method for treating abnormal levels of Myc, the method comprising administering an oligomer of the disclosure, or a conjugate or a pharmaceutical composition thereof, to a patient in need of such treatment, and further comprising the administration of a further chemotherapeutic agent. In some embodiments, the chemotherapeutic agent is conjugated to the oligomer, is present in the pharmaceutical composition, or is administered in a separate formulation.

The disclosure also relates to an oligomer, a composition or a conjugate as defined herein for use as a medicament.

The disclosure further relates to use of a compound, composition, or a conjugate as defined herein for the manufacture of a medicament for the treatment of abnormal levels of Myc or expression of mutant forms of Myc (such as allelic variants, such as those associated with one of the diseases referred to herein).

Suitable dosages, formulations, administration routes, compositions, dosage forms, combinations with other therapeutic agents, pro-drug formulations are also provided in PCT/DK2006/000512, which is hereby incorporated by reference.

The disclosure also provides for a pharmaceutical composition comprising a compound or a conjugate as herein described or a conjugate, and a pharmaceutically acceptable diluent, carrier or adjuvant. PCT/DK2006/000512 provides suitable and preferred pharmaceutically acceptable diluents, carriers and adjuvants—which are hereby incorporated by reference.

In accordance with the present disclosure, a series of oligomers were designed to target different regions of human c-Myc mRNA (GenBank Accession number NM_002467.4; SEQ ID NO: 1) and human N-Myc mRNA (GenBank Accession number NM_005378.4).

SEQ ID NOs: 3-25, shown in Table 2, below, are sequences of oligomers designed to target human c-Myc mRNA and human N-Myc RNA. The target region of the c-Myc target nucleic acid is indicated in the table.

TABLE 2

Antisense Oligonucleotide Sequences

| SEQ ID NO | Sequence (5'-3') | Length (bases) | Target site NM_ 002467.4 |
| --- | --- | --- | --- |
| SEQ ID NO: 3 | AGTTCCTGTTGGTGAA | 16 | 589-604 |
| SEQ ID NO: 4 | TCACCATGTCTCCTCC | 16 | 889-904 |
| SEQ ID NO: 5 | TTCACCATGTCTCCTC | 16 | 890-905 |
| SEQ ID NO: 6 | GGTTCACCATGTCTCC | 16 | 892-907 |
| SEQ ID NO: 7 | TACAGTCCTGGATGAT | 16 | 955-970 |
| SEQ ID NO: 8 | CATACAGTCCTGGATG | 16 | 957-972 |
| SEQ ID NO: 9 | TGTTGGTGAAGCTAAC | 16 | 583-598 |
| SEQ ID NO: 10 | CTGTTGGTGAAGCTAA | 16 | 584-599 |
| SEQ ID NO: 11 | GGTACAAGCTGGAGGT | 16 | 1087-1102 |
| SEQ ID NO: 12 | GTGAGGAGGTTTGCTG | 16 | 1431-1446 |
| SEQ ID NO: 13 | TGTGAGGAGGTTTGCT | 16 | 1432-1447 |
| SEQ ID NO: 14 | TAGTTGTGCTGATGTG | 16 | 1481-1496 |
| SEQ ID NO: 15 | GTAGTTGTGCTGATGT | 16 | 1482-1497 |
| SEQ ID NO: 16 | GACACTGTCCAACTTG | 16 | 1545-1560 |
| SEQ ID NO: 17 | TCAGGACTCTGACACT | 16 | 1555-1570 |
| SEQ ID NO: 18 | CTCAGGACTCTGACAC | 16 | 1556-1571 |
| SEQ ID NO: 19 | ATCTGTCTCAGGACTC | 16 | 1562-1577 |
| SEQ ID NO: 20 | GATCTGTCTCAGGACT | 16 | 1563-1578 |
| SEQ ID NO: 21 | TGATCTGTCTCAGGAC | 16 | 1564-1579 |
| SEQ ID NO: 22 | AGGATAACTACCTTGG | 16 | 1742-1757 |
| SEQ ID NO: 23 | GACAGGATGTATGCTG | 16 | 1769-1784 |
| SEQ ID NO: 24 | GGACAGGATGTATGCT | 16 | 1170-1785 |
| SEQ ID NO: 25 | GCTGTTCAAGTTTGTG | 16 | 1855-1870 |

12. Examples

12.1. Example 1

LNA Phosphoramidites Synthesis

The LNA phosphoramidites were synthesized according to the method described in WO07/031,081. Methyl-cytidine LNA phosphoramidite was used to incorporate into sequences by solid-phase synthesis approach.

12.2. Example 2

LNA Oligonucleotide Synthesis

Antisense c-Myc oligonucleotides (SEQ ID NOs: 26-48) shown in Table 3 were synthesized using standard solid-phase DNA/RNA phosphoramidite chemistry approach on an Akta Oligopilot 10 DNA/RNA synthesizer at 40 μmol scale using NittoPhase Unylinker solid support. Detritylation step during solid-phase synthesis was performed with 3% dichloroacetic acid (DCA) in toluene (v/v). The coupling step was carried out with 0.3M solution of -5-(benzylthio)-1H-tetrzole in dry acetonitrile for 5 min and 10 min recycle time for DNA and LNA, respectively. The sulfurization step was carried out using 0.2 M xanthanehydride (XH) in pyridine for 3 min on the solid support. The capping step on the solid-phase was carried out with 1:1 mixture NMI and isobuyric anydride in Lutidne. After final detritylation at 5'-end, solid support was treated with 20% diethylamine (DEA) in dry acetonitrile for 10 min on the synthesizer. Cleavage and base deprotection was carried out in a single step using concentrated aqueous ammonia for 16 h at 55° C. After cleavage and deprotection, the reaction mixture was cooled at 4° C. for 30 minutes and filtered to remove the solid support.

Crude c-Myc LNA/DNA gapmer oligonucleotides thus synthesized were characterized by ion-pair high performance liquid chromatography and mass-spectrometry (reversed-phase and electro spray-ionization mass spectrometry). C-Myc oligonucleotides with correct full length sequence and molecular weight were taken to the next step of further work up. The oligonucleotides were concentrated to remove excess ammonium hydroxide and dissolved in ~300 mM sodium acetate at pH 5.2. The oligonucleotides with full-length correct sequence were precipitated with standard ethanol precipitation. Precipitation was carried out with the addition of 3 to 4 sample volumes of cold ethanol and centrifugation at 3000 rpm at −40° C. The pellet obtained by centrifuging was washed twice with cold ethanol to remove residual protecting groups from deprotection step and dried. The dried pellet was re-dissolved in WFI and quantified by UV at 260 nm. An aliquot of ~10 to 15 mg of each c-Myc oligonucleotide was pipetted into a 10 ml sterile Falcon tube and lyophilized. Each of the final oligonucleotides was analyzed by HPLC prior to high content screening. Results of solid-phase synthesis of c-Myc LNA/DNA gapmer oligonucleotides including their HPLC purity and identification by LC-MS are included in Table 3.

In Table 3, upper case, boldface capital letters indicate nucleoside analogue monomers (e.g., β-D-oxy LNA monomers) and lower case letters represent DNA monomers. Subscript "s" represents phosphorothioate linkage groups between the monomers. All cytosine bases in the LNA monomers are 5-methylcytosines.

Potent oligonucleotide sequences 28, 34 and 39 from screening studies were further synthesized at 1 to 4 grams scale on Nittophase™ UnyLinker (NP Unylinker) solid support for use in further evaluation in cell culture and Xenograft studies. Three 1 millimol scale syntheses were performed and crude sample obtained from each synthesis was processed through purification, desalting and freeze drying steps to obtain 1 to 4 grams of compounds for further investigation in tumor bearing mice. Results showed all three syntheses gave comparable crude in terms of % FLP by RP HPLC and yield. All three syntheses were processed through purification, desalting and freeze-drying (FD) to deliver two ~1 g lots of solid active pharmaceutical ingredient (API).

TABLE 3

| SEQ ID NO | Sequence (5'-3') | Theoretical Molecular Weight (Da) | Theoretical Molar Extinction Co-Efficient L(mole*cm) | Measured Molecular Weight (Da) | Purity By Measured by HPLC Area (%) | Yield (%) |
|---|---|---|---|---|---|---|
| SEQ ID NO: 26 | A$_s$G$_s$T$_s$t$_s$c$_s$c$_s$t$_s$g$_s$t$_s$t$_s$g$_s$g$_s$t$_s$G$_s$A$_s$A | 5,336.20 | 155,900.00 | 5334 | 86.1 | 53.54 |
| SEQ ID NO: 27 | T$_s$C$_s$A$_s$c$_s$c$_s$a$_s$t$_s$g$_s$t$_s$c$_s$t$_s$c$_s$c$_s$T$_s$C$_s$C | 5,179.20 | 135,500.00 | 5178 | 89.0 | 72.54 |
| SEQ ID NO: 28 | T$_s$T$_s$C$_s$a$_s$c$_s$c$_s$a$_s$t$_s$g$_s$t$_s$c$_s$t$_s$c$_s$c$_s$C$_s$T$_s$C | 5,194.20 | 136,400.00 | 5193 | 89.4 | 55.44 |
| SEQ ID NO: 29 | G$_s$G$_s$T$_s$t$_s$c$_s$a$_s$c$_s$c$_s$a$_s$t$_s$g$_s$t$_s$c$_s$t$_s$C$_s$T$_s$C | 5,245.20 | 142,500.00 | 5244 | 85.7 | 65.82 |
| SEQ ID NO: 30 | T$_s$A$_s$C$_s$a$_s$g$_s$t$_s$c$_s$c$_s$t$_s$g$_s$g$_s$a$_s$t$_s$G$_s$A$_s$T | 5,319.20 | 156,500.00 | 5318 | 88.4 | 67.20 |
| SEQ ID NO: 31 | C$_s$A$_s$T$_s$a$_s$c$_s$a$_s$g$_s$t$_s$c$_s$c$_s$t$_s$g$_s$g$_s$A$_s$T$_s$G | 5,304.20 | 155,300.00 | 5302 | 85.4 | 60.23 |
| SEQ ID NO: 32 | T$_s$G$_s$T$_s$t$_s$g$_s$g$_s$t$_s$g$_s$a$_s$a$_s$g$_s$c$_s$t$_s$A$_s$A$_s$C | 5,359.30 | 156,500.00 | 5358 | 85.2 | 68.71 |
| SEQ ID NO: 33 | C$_s$T$_s$G$_s$t$_s$t$_s$g$_s$g$_s$t$_s$g$_s$a$_s$a$_s$g$_s$c$_s$T$_s$A$_s$A | 5,359.30 | 157,200.00 | 5357 | 83.3 | 65.07 |
| SEQ ID NO: 34 | G$_s$G$_s$T$_s$a$_s$c$_s$a$_s$a$_s$g$_s$c$_s$t$_s$g$_s$g$_s$a$_s$G$_s$G$_s$T | 5,395.30 | 162,200.00 | 5394 | 89.1 | 62.83 |
| SEQ ID NO: 35 | G$_s$T$_s$G$_s$a$_s$g$_s$g$_s$a$_s$g$_s$g$_s$t$_s$t$_s$t$_s$g$_s$C$_s$T$_s$G | 5,431.30 | 156,300.00 | 5430 | 86.3 | 68.16 |
| SEQ ID NO: 36 | T$_s$G$_s$T$_s$g$_s$a$_s$g$_s$g$_s$a$_s$g$_s$g$_s$t$_s$t$_s$t$_s$G$_s$C$_s$T | 5,406.30 | 153,500.00 | 5404 | 81.6 | 72.78 |
| SEQ ID NO: 37 | T$_s$A$_s$G$_s$t$_s$t$_s$g$_s$t$_s$g$_s$c$_s$t$_s$g$_s$a$_s$t$_s$G$_s$T$_s$G | 5,367.20 | 153,100.00 | 5365 | 87.6 | 74.29 |
| SEQ ID NO: 38 | G$_s$T$_s$A$_s$g$_s$t$_s$t$_s$g$_s$t$_s$g$_s$c$_s$t$_s$g$_s$a$_s$T$_s$G$_s$T | 5,367.20 | 154,100.00 | 5365 | 89.4 | 64.88 |
| SEQ ID NO: 39 | G$_s$A$_s$C$_s$a$_s$c$_s$t$_s$g$_s$t$_s$c$_s$c$_s$a$_s$a$_s$c$_s$T$_s$T$_s$G | 5,264.20 | 149,700.00 | 5262 | 90.6 | 60.45 |
| SEQ ID NO: 40 | T$_s$C$_s$A$_s$g$_s$g$_s$a$_s$c$_s$t$_s$c$_s$t$_s$g$_s$a$_s$c$_s$A$_s$C$_s$T | 5,278.20 | 149,500.00 | 5276 | 87.1 | 59.25 |
| SEQ ID NO: 41 | C$_s$T$_s$C$_s$a$_s$g$_s$g$_s$a$_s$c$_s$t$_s$c$_s$t$_s$g$_s$a$_s$C$_s$A$_s$C | 5,291.30 | 148,200.00 | 5290 | 89.5 | 57.50 |
| SEQ ID NO: 42 | A$_s$T$_s$C$_s$t$_s$g$_s$t$_s$c$_s$t$_s$c$_s$a$_s$g$_s$g$_s$a$_s$C$_s$T$_s$C | 5,283.20 | 148,000.00 | 5282 | 89.1 | 66.05 |
| SEQ ID NO: 43 | G$_s$A$_s$T$_s$c$_s$t$_s$g$_s$t$_s$c$_s$t$_s$c$_s$a$_s$g$_s$g$_s$A$_s$C$_s$T | 5,295.20 | 150,300.00 | 5296 | 88.6 | 66.94 |
| SEQ ID NO: 44 | T$_s$G$_s$A$_s$t$_s$c$_s$t$_s$g$_s$t$_s$c$_s$t$_s$c$_s$a$_s$g$_s$g$_s$G$_s$A$_s$C | 5,295.20 | 150,000.00 | 5294 | 89.3 | 67.13 |
| SEQ ID NO: 45 | A$_s$G$_s$G$_s$a$_s$t$_s$a$_s$a$_s$c$_s$t$_s$a$_s$c$_s$c$_s$t$_s$T$_s$G$_s$G | 5,314.20 | 160,500.00 | 5313 | 83.2 | 61.95 |
| SEQ ID NO: 46 | G$_s$A$_s$C$_s$a$_s$g$_s$g$_s$a$_s$t$_s$g$_s$t$_s$a$_s$t$_s$g$_s$C$_s$T$_s$G | 5,398.30 | 161,000.00 | 5397 | 88.9 | 57.05 |
| SEQ ID NO: 47 | G$_s$G$_s$A$_s$c$_s$a$_s$g$_s$g$_s$a$_s$t$_s$g$_s$t$_s$a$_s$t$_s$G$_s$C$_s$T | 5,384.30 | 160,800.00 | 5383 | 83.5 | 59.38 |
| SEQ ID NO: 48 | G$_s$C$_s$T$_s$g$_s$t$_s$t$_s$c$_s$a$_s$a$_s$g$_s$t$_s$t$_s$t$_s$G$_s$T$_s$G | 5,341.20 | 149,000.00 | 5340 | 89.5 | 67.63 |

12.3. Example 3

Preparation of Conjugates of Oligomers with Polyethylene Glycol

The oligomers having sequences shown as SEQ ID NO: 32 or SEQ ID NO: 39 are functionalized on the 5' terminus by attaching an aminoalkyl group, such as hexan-1-amine blocked with a blocking group such as Fmoc to the 5' phosphate groups of the oligomers using routine phosphoramidite chemistry, oxidizing the resultant compounds, deprotecting them and purifying them to achieve the functionalized oligomers, respectively, having the formulas (IA) and (IB):

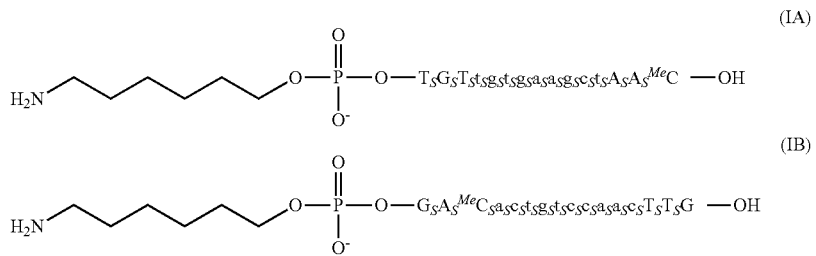

wherein the bold uppercase letters represent nucleoside analogue monomers, lowercase letters represent DNA monomers, the subscript "s" represents a phosphorothioate linkage, and $^{Me}C$ represents 5-methylcytosine.

A solution of activated PEG, such as the one shown in formula (II):

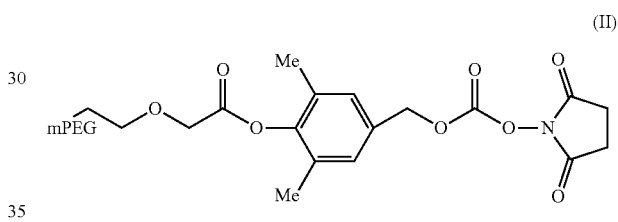

wherein the PEG moiety has an average molecular weight of 12,000, and each of the compounds of formulas (IA) and (IB) in PBS buffer are stirred in separate vessels at room temperature for 12 hours. The reaction solutions are extracted three times with methylene chloride and the combined organic layers are dried over magnesium sulphate and filtered and the solvent is evaporated under reduced pressure. The resulting residues are dissolved in double distilled water and loaded onto an anion exchange column. Unreacted PEG linker is eluted with water and the products are eluted with $NH_4HCO_3$ solution. Fractions containing pure products are pooled and lyophilized to yield the conjugates SEQ ID NOs: 32 and 39, respectively as show in formulas (IIIA) and (IIIB):

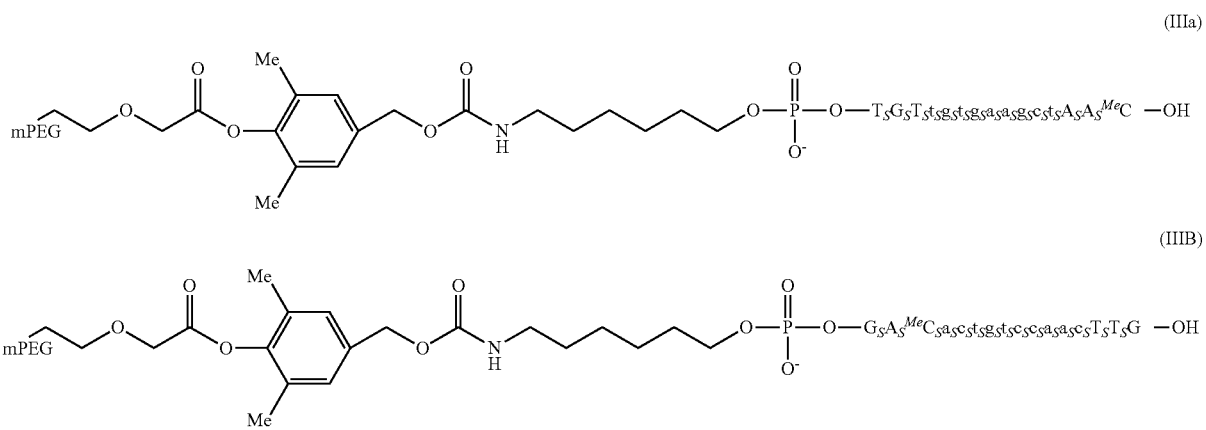

wherein each of the oligomers of SEQ ID NOs: 32 and 39 is attached to a PEG polymer having average molecular weight of 12,000 via a releasable linker.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

12.4. Example 4

In Vitro Model: Transfection with Antisense Oligomers

Cells were treated with oligomers using the cationic liposome formulation LipofectAMINE 2000 (Gibco) as transfection vehicle. Formulation of olignucleotide-lipid complexes were carried out essentially as described by the manufacturer using serum-free OptiMEM (Gibco) and a final lipid concentration of 5 µg/ml LipofectAMINE 2000. Cells were incubated at 37° C. for 4 hours and the transfection treatment was stopped by removal of the oligonucleotide-containing culture medium. Cells were washed and serum-containing medium was added.

12.5. Example 5

Figure 1B:
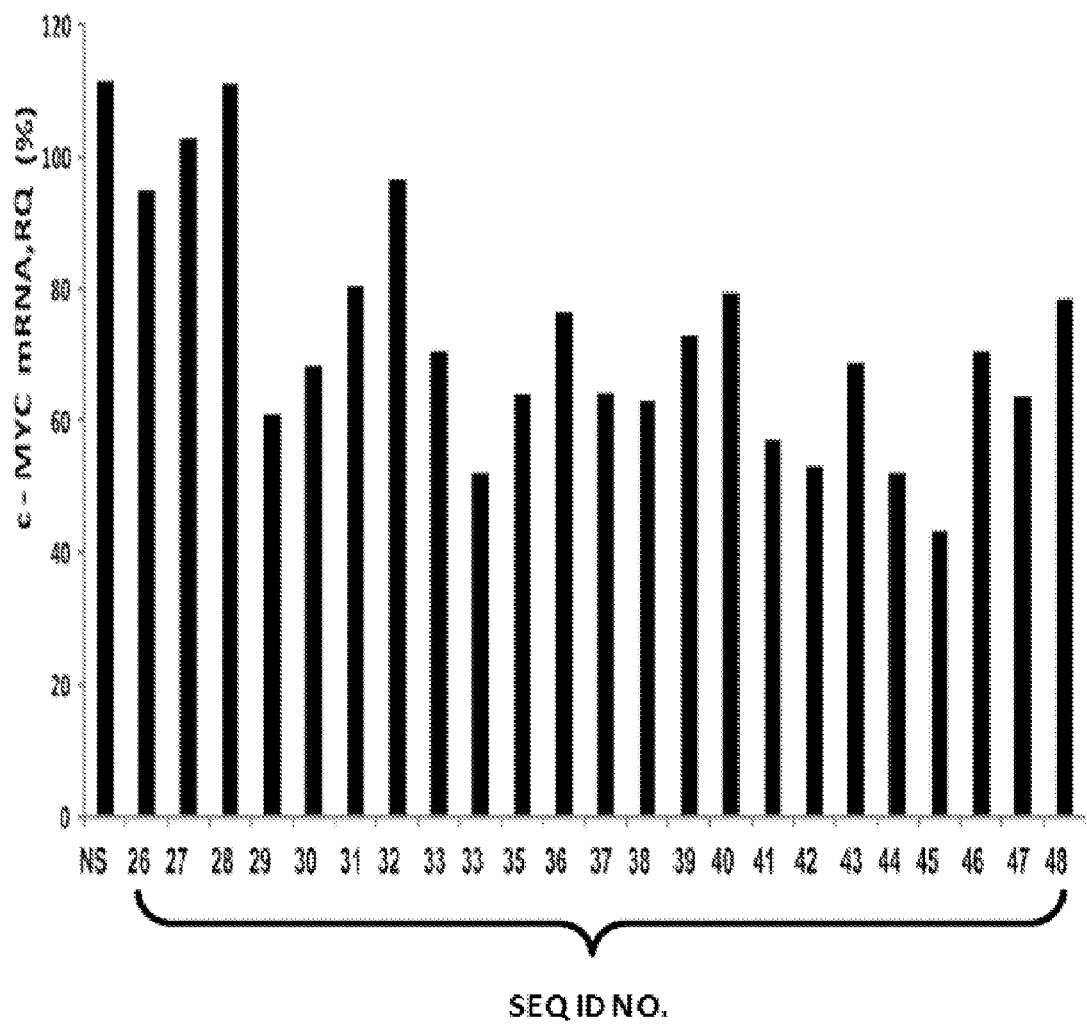
FIG. 1B is a graph showing c-Myc mRNA down regulation in SKBr3 breast cancer cells in response to the LNA oligomers represented by SEQ ID NOs: 26-48.

Effect of Oligonucleotides on c-Myc mRNA Expression in MM1.S Multiple Myeloma Cells and SKBr3 Breast Cancer Cells without Transfection Antisense c-Myc oligonucleotides as shown in Table 3 were evaluated for their ability to downregulate c-Myc mRNA expression. Specifically, MM1.S multiple myeloma cells were plated (800/well) in 12-well cell culture plates and treated for 72 hours with antisense oligonucleotides at a final concentration of 10 µM. After treatment, cells were harvested and qRT-PCR performed to measure the relative level of c-Myc mRNA. A non-specific oligonucleotide (NS) was used as a negative control. Signals for c-Myc mRNA were normalized to that of 18S rRNA (See FIGS. 1A and 1B).

12.5.1 Extraction of RNA and cDNA Synthesis

Total RNA was extracted from cells treated as described above using the Qiagen RNeasy® kit (Qiagen Cat. #74104) according to the manufacturer's instructions. First strand synthesis was performed using reverse transcriptase reagents from Ambion according to the manufacturer's instructions.

For each sample, 0.5 µg of RNA was adjusted to 10.8 µl total volume with RNase-free $H_2O$ and mixed with 2 µl of random decamers (50 µM) and 4 µl of dNTP mix (2.5 mM of each dNTP) and heated to 70° C. for 3 minutes. Samples were then rapidly cooled on ice. After cooling, 2 µl of 10× Buffer RT, 1 µl MMLV Reverse Transcriptase (100 U/µl), and 0.25 µl RNase inhibitor (10 U/µl) were added to each sample. Samples were incubated at 42° C. for 60 minutes followed by heat inactivation of the enzyme at 95° C. for 10 minutes. Samples were then cooled to 4° C.

12.5.2 q-RT-PCR

The sample content of c-Myc was quantified as follows: The cDNA from 12.4.1 was diluted 5-fold with water, and 8 µl of diluted cDNA was added to each reaction. The qPCR reaction was conducted using the protocol provided in the TaqMan® Gene Expression Master Mix kit according to manufacturer's instruction. A Master Mix was prepared for each qPCR reaction as shown below. A cDNA template was then added to each tube. The PCR reaction was performed according to manufacturer-suggested cycle conditions.

Preparation of qPCR Reaction Mixture

| Component | Volume (µL)/ 20 µl Reaction |
| --- | --- |
| TaqMan Gene Expression Master Mix (2×) | 10 |
| TaqMan Gene Expression Assay (20×) | 1 |
| cDNA dilution | 8 |
| $dH_2O$ | 1 |
| Total Volume | 20 |

12.6 Example 6

Figure 2A:
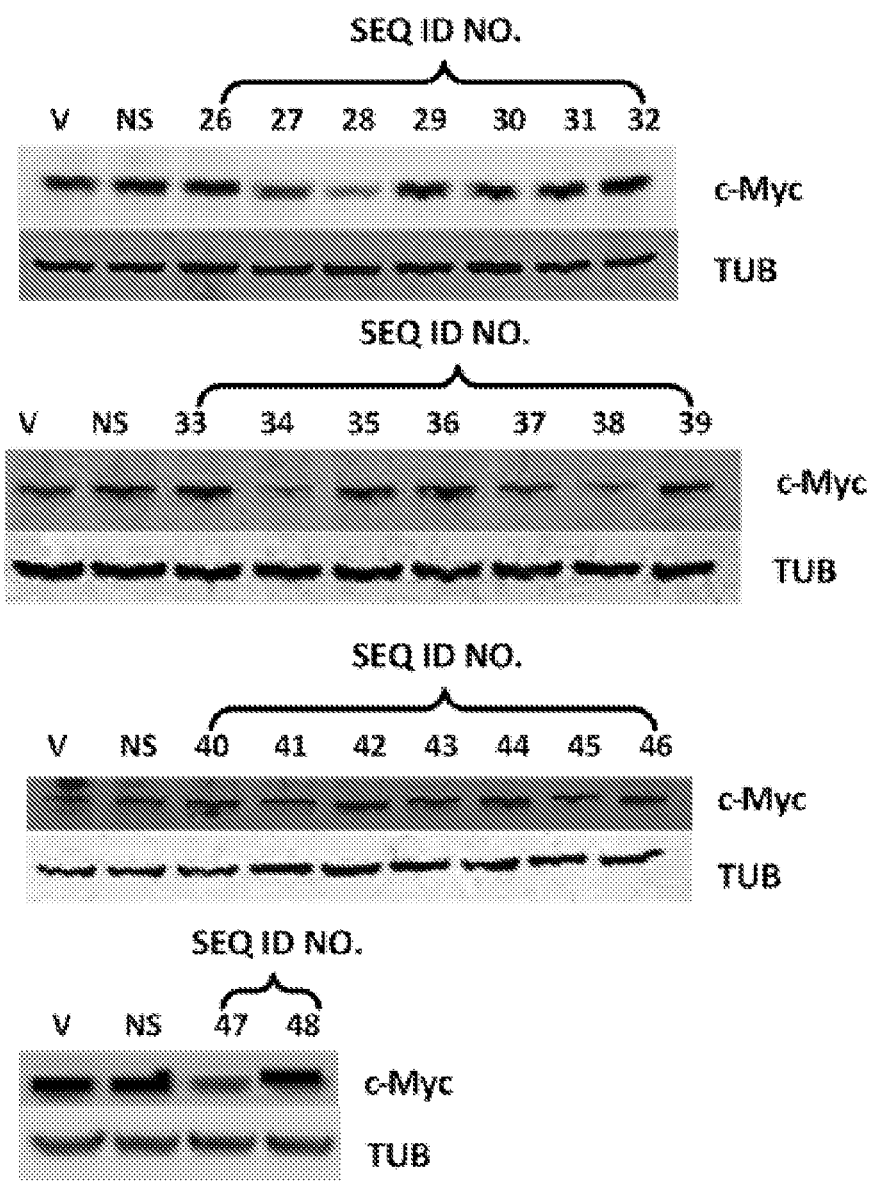
FIG. 2A shows c-Myc protein down-regulation in MM1.S human multiple myeloma cells treated with LNA oligomers represented by SEQ ID NOs: 26-48.
Figure 2B:
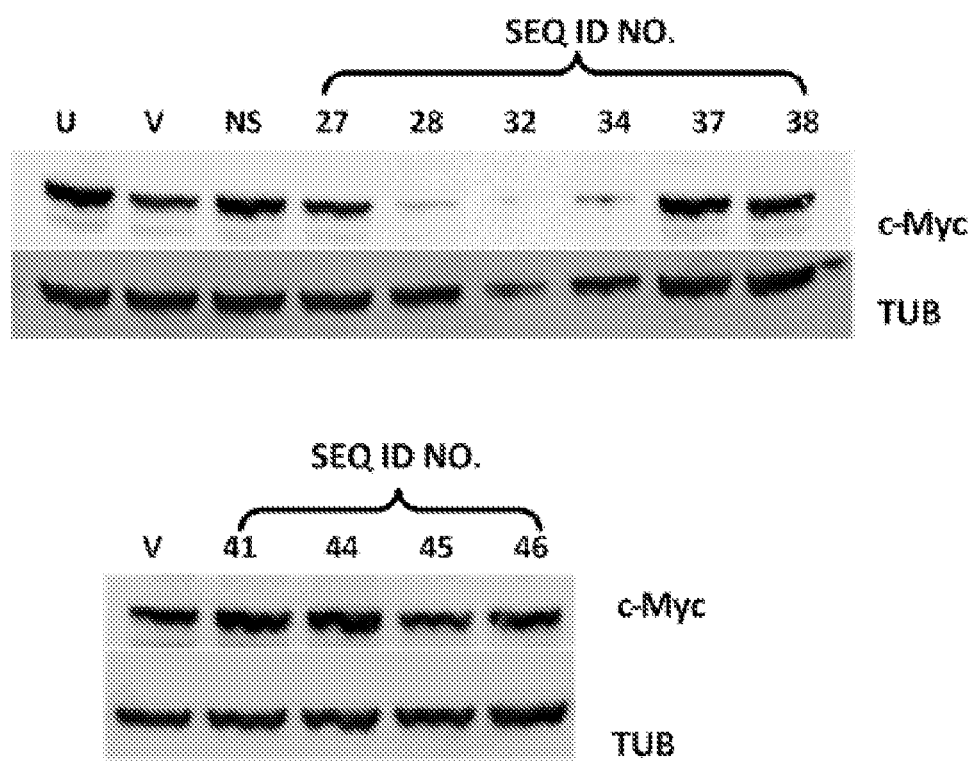
FIG. 2B shows c-Myc protein down-regulation in HEPG2 human hepatocellular carcinoma cells treated with LNA oligomers represented by the indicated SEQ ID NOs.
Figure 2C:
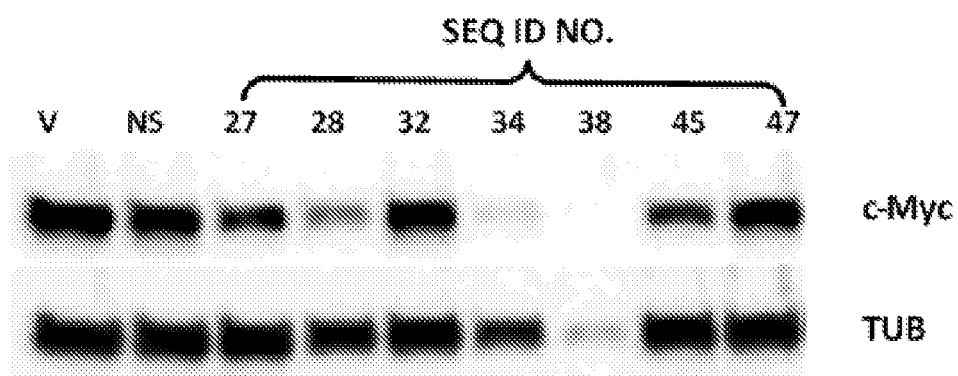
FIG. 2C shows c-Myc protein down-regulation in CUTTL1 human T-cell acute lymphoblastic leukemia cells treated with LNA oligomers represented by the indicated SEQ ID NOs.

Effect of Oligonucleotides on c-Myc Protein Expression in Multiple Myeloma Cells, Hepatocellular Carcinoma Cells, and T-Cell Acute Lymphoblastic Leukemia Cells without Transfection Antisense c-Myc oligonucleotides as shown in Table 3 were evaluated for their ability to downregulate c-Myc protein expression. Specifically, MM1.S human multiple myeloma cells, HEPG2 human hepatocellular carcinoma cells, and CUTTL1 human T-cell acute lymphoblastic leukemia cells were plated onto 6-well cell culture plates and treated for 72 hours with antisense oligonucleotides at a final concentration of 10 µM. After treatment, cells were harvested and lysed in RIPA buffer. Equal amounts of total cellular protein (50 µg/well) were loaded onto 4-12% acrylimide gel. Gels were transferred to blotting membrane with iBlot semi-dry transfer system (Invitrogen). The membrane was blocked with a solution of 5% milk/TBS-Tween. Total cellular c-Myc was detected using an antibody specific to c-Myc protein (Santa Cruz Biotech, sc-764). HRP-linked secondary antibodies were used for chemiluminescent detection. After c-Myc protein detection, blots were stripped and incubated with an antibody specific to alpha tubule (Sigma, T-5168). Alpha-tubule (TUB) was used as a loading control. See FIGS. 2A, 2B, and 2C. V represents vehicle-treated cells. The vehicle was 50% PBS, 50% DMSO. NS represents cells treated with a non-specific antisense oligonucleotide.

12.7. Example 7

Figure 3:
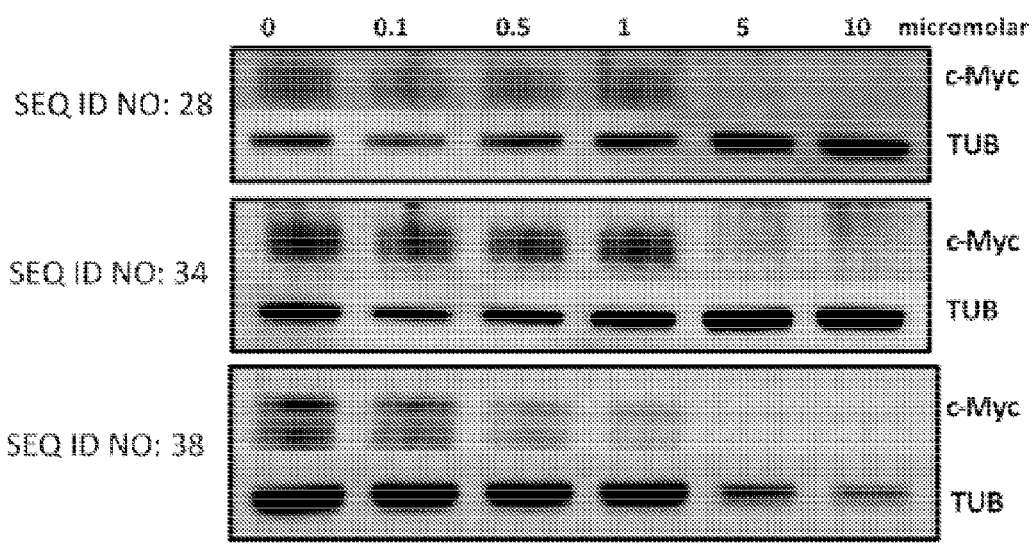
FIG. 3 shows the relative potency of three select Myc LNA oligomers with regard to their ability to inhibit c-Myc protein expression in MM1.S human multiple myeloma cells. MM1.S cells were treated with the LNA oligonucleotides represented by SEQ ID NOs: 28, 34, or 38 at the indicated concentrations.

Concentration Response Relationship of Oligonucleotides on c-Myc Protein Expression in Multiple Myeloma Cells without Transfection Antisense c-Myc oligonucleotides representing SEQ ID NOS: 28, 34, and 38 were evaluated for their potency with regard to their ability to inhibit c-Myc protein expression in multiple myeloma cells. MM1.S human multiple myeloma cells were plated onto 6-well cell culture plates and treated for 72 hours with increasing concentrations of c-Myc oligonucleotides represented by SEQ ID NO: 28, 34, or 38 as shown in Table 3. Cells were then harvested and lysed for immunoblot detection of total cellular c-Myc protein levels as described in Example 6. See FIG. 3.

12.8. Example 8

Effect of Oligonucleotides on Apoptosis in Multiple Myeloma, Hepatocellular Carcinoma, and T-Cell Acute Lymphoblastic Leukemia Cells without Transfection Antisense c-Myc oligonucleotides as shown in Table 3 were evaluated for their ability to induce apoptosis in multiple myeloma cells, hepatocellular carcinoma cells, and T-cell acute lymphoblastic leukemia cells. Caspases 3 and 7 activities were measured as an indicator of apoptosis in response to Myc oligonucleotides. Specifically, MM1.S human multiple myeloma cells, HEPG2 human hepatocellular carcinoma cells, and CUTTL1 human T-cell acute lymphoblastic leukemia cells were plated in (40,000/well) 96-well cell culture plates. Cells were treated for 72 hours with antisense oligonucleotides at a final concentration of 10 µM. Cells were then harvested and caspases 3 and 7 activities were detected using the Caspase-Glo® 3/7 assay kit (Promega) as described below.

12.8.1. Caspase Assay

Figure 4A:
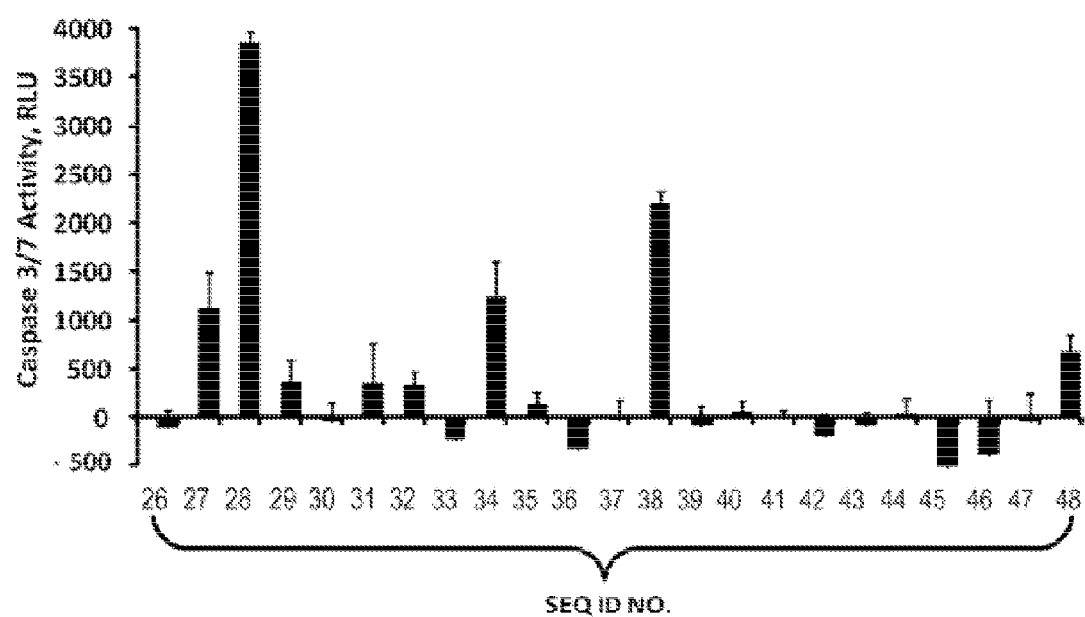
FIG. 4A shows the effect of LNA oligomers represented by SEQ ID NOs: 26-48 on apoptosis of MM1.S human multiple myeloma cells. Caspases 3 and 7 were measured as indicators of apoptosis.
Figure 4B:
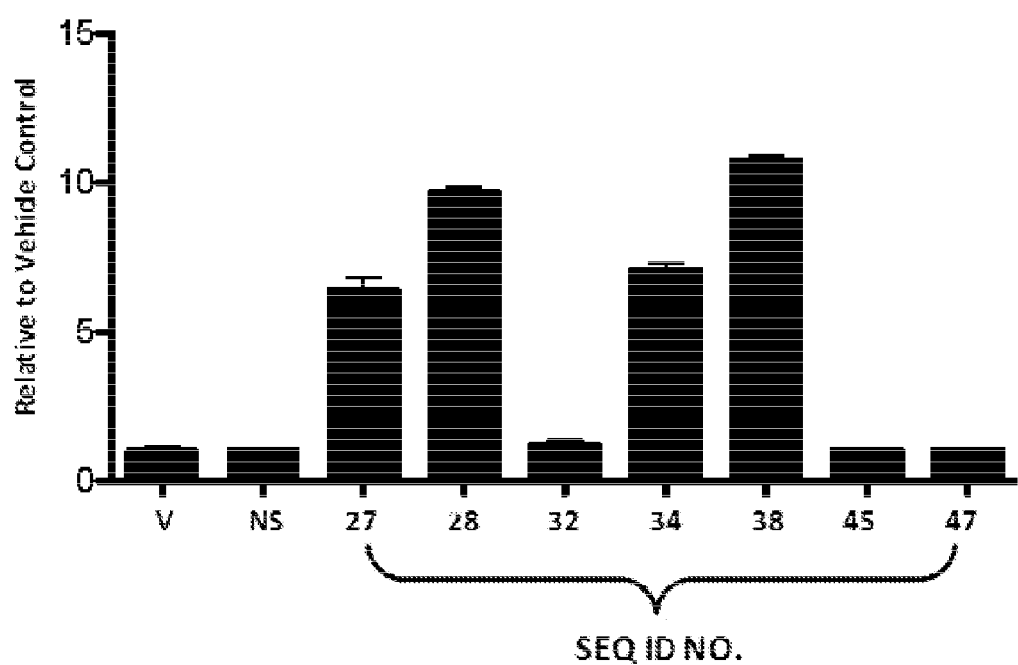
FIG. 4B shows the effect of LNA oligomers represented by the indicated SEQ ID NOs on apoptosis of CUTTL1 human T-cell acute lymphoblastic leukemia cells. Caspases 3 and 7 were measured as indicators of apoptosis as in FIG. 4A.

The activity of apoptosis specific caspases 3 and 7 was measured using a luminogenic Caspase-Glo® 3/7 substrate assay (Cat # G8091, Promega). The plate to be analyzed was equilibrated to room temperature for 15 minutes. The Caspase-Glo® 3/7 buffer was mixed with the Caspase-Glo® 3/7 substrate to form a working solution which was equilibrated to room temperature. Then, 100 µl of the working solution were added to the medium in each well of the 96-well cell culture plate. The plate was shaken for 1 minute then incubated at room temperature for 1 hour protected from light. The caspase activity was measured as Relative Light Units per second (RLU/s) in a Luminoscan Ascent instrument (Thermo Labsystems). See FIGS. 4A, 4B. Error bars represent standard deviation (n=3).

12.9. Example 9

Figure 4C:
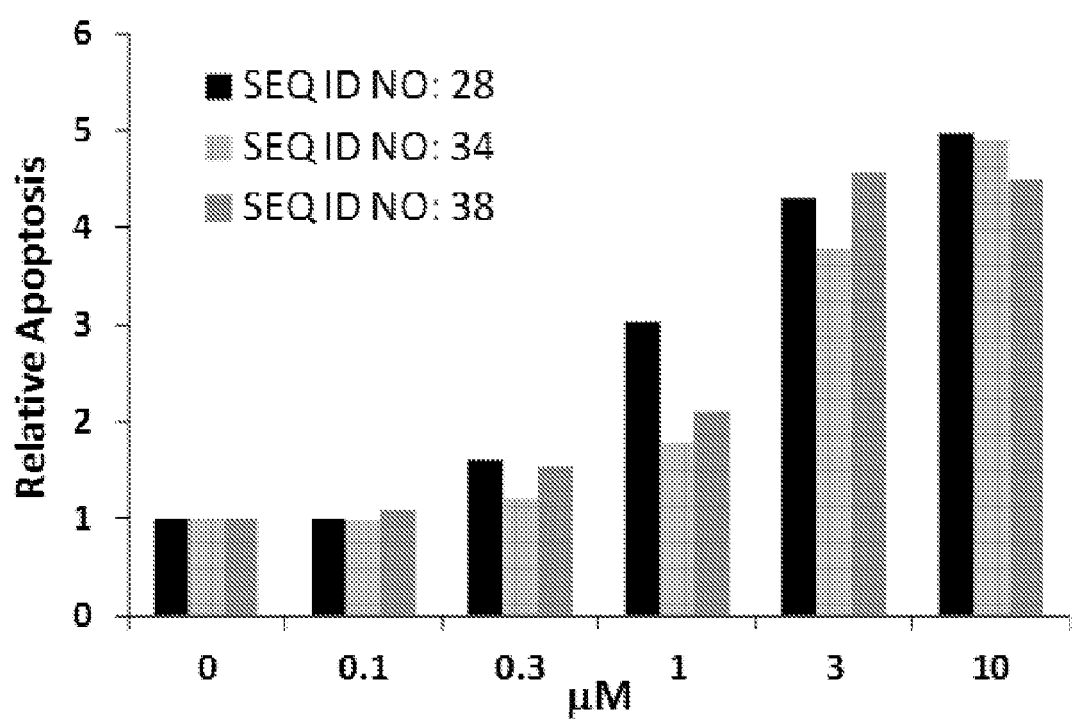
FIG. 4C shows the relative potency of three select LNA oligomers represented by SEQ ID NOs: 28, 34, or 38 with regard to their ability to induce apoptosis in MM1.S human multiple myeloma cells. Cells were transfected with the LNA oligomers at the indicated concentrations and caspases 3 and 7 activities were detected as an indicator of apoptosis.

Concentration Response Relationship of Oligonucleotides on Apoptosis in Multiple Myeloma Cells Antisense c-Myc oligonucleotides representing SEQ ID NOs: 28, 34, and 38 were evaluated for their potency with regard to their ability to induce apoptosis in multiple myeloma cells. MM1.S human multiple myeloma cells were plated onto 96-well cell culture plates (40,000/well) and treated for 72 hours with indicated concentrations of antisense oligonucleotides. Cells were harvested and caspase –3 and –7 activities were measured as an indicator of apoptosis in response to c-Myc oligonucleotides as in Example 8. See FIG. 4C. Data are the average of two wells.

12.10. Example 10

Figure 5A:
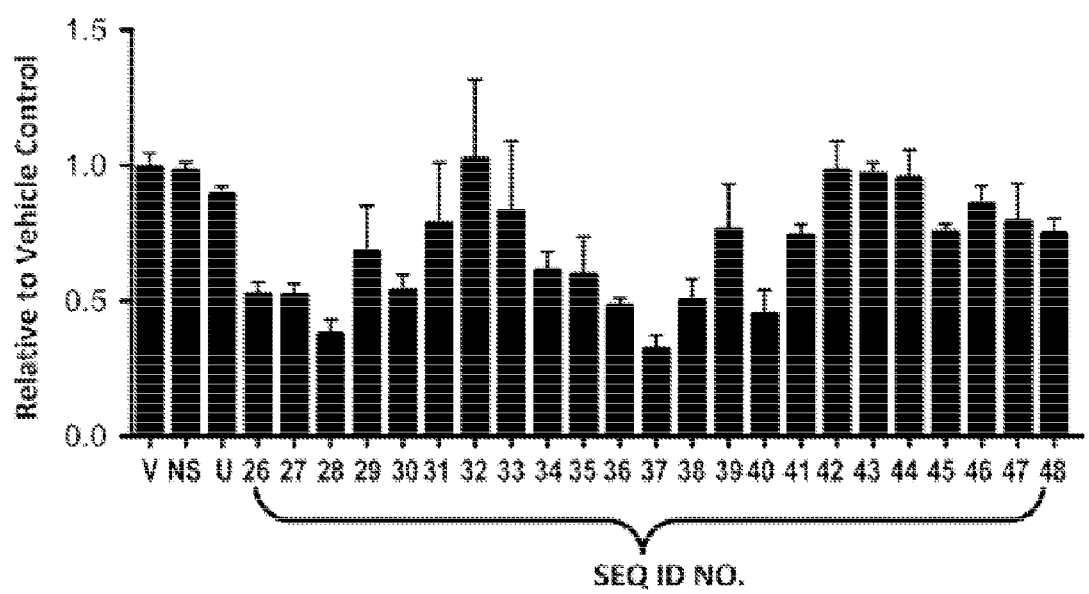
FIG. 5A is a graph representing inhibition of MM1.S human multiple myeloma cell proliferation by LNA oligomers represented by SEQ ID NOs: 26-48. ATP levels, as an indicator of cell proliferation are presented
Figure 5B:
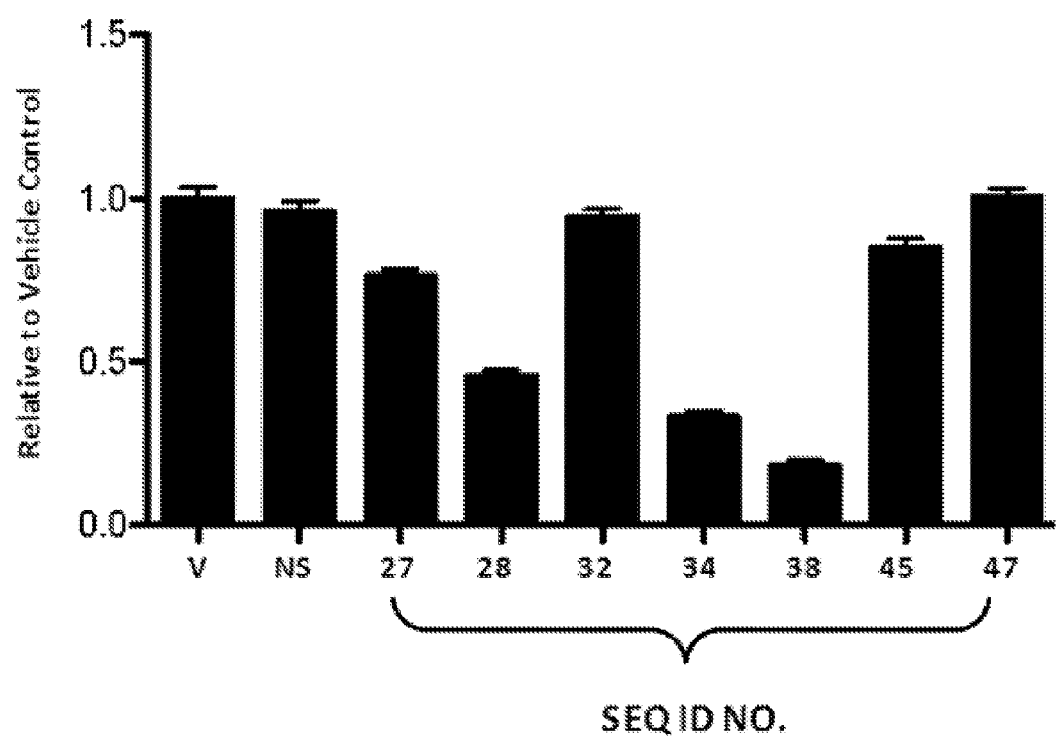
FIG. 5B is a graph representing inhibition of CUTTL1 human T-cell acute lymphoblastic leukemia cell proliferation by LNA oligomers represented by the indicated SEQ ID NOs.

Effect of Oligonucleotides on Proliferation and Cytotoxicity in Multiple Myeloma and T-Cell Acute Lymphoblastic Leukemia Cells Antisense c-Myc oligonucleotides as shown in Table 3 were evaluated for their ability to inhibit cellular proliferation in multiple myeloma cells and T-cell acute lymphoblastic leukemia cells. ATP levels were measured as a known indicator of proliferation and cytotoxicity. MM1.S human multiple myeloma cells and CUTTL1 human T-cell acute lymphoblastic leukemia cells were plated onto 6-well cell culture plates and treated for 72 hours with antisense oligonucleotides at a final concentration of 10 µM. Cells were then harvested and ATP levels were detected using a chemiluminescent reagent (ATPlite™, Perkin-Elmer) in a 384 well plate. Cells/media (50 µl) were added to each well followed by 25 ul/well of ATPlite™. The plate was incubated for 15 minutes at room temperature, and chemiluminescent signal was read on an Envision plate reader (Perkin-Elmer). See FIGS. 5A and 5B. ATP levels are presented relative to vehicle-treated cells (V). A non-specific oligonucleotide (NS) was used as a negative control. U in FIG. 5A represents untreated cells. Error bars represent standard deviation, n=3.

12.11. Example 11

Figure 5C:
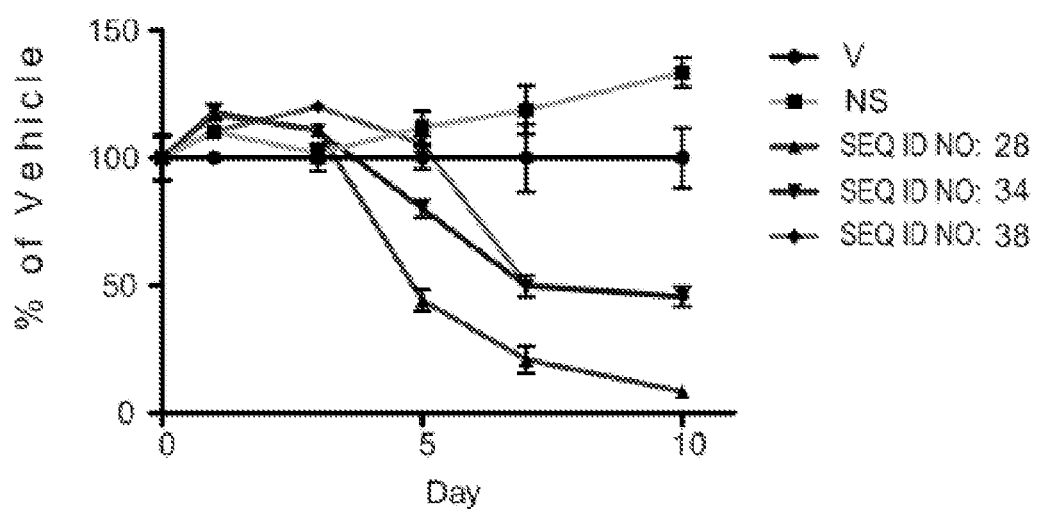
FIG. 5C is a graph representing inhibition of MM1.S multiple myeloma cell proliferation over time in response to three select LNA oligomers represented by SEQ ID NOs: 28, 34, and 38.
Figure 6A:
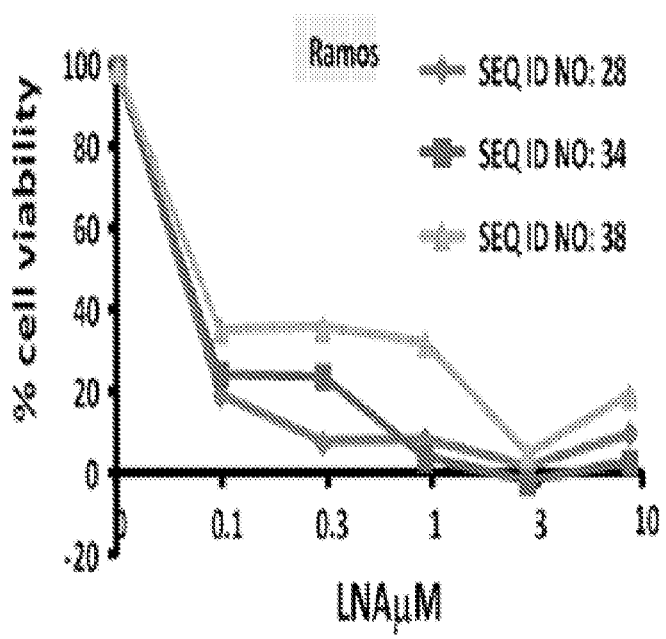
FIG. 6A is a graph representing the relative potency of LNA oligomers represented by SEQ ID NOs: 28, 34, and 38 with regard to their ability to inhibit proliferation of Ramos human Burkitt's lymphoma cells. ATP levels were detected as an indicator of cell proliferation.
Figure 6B:
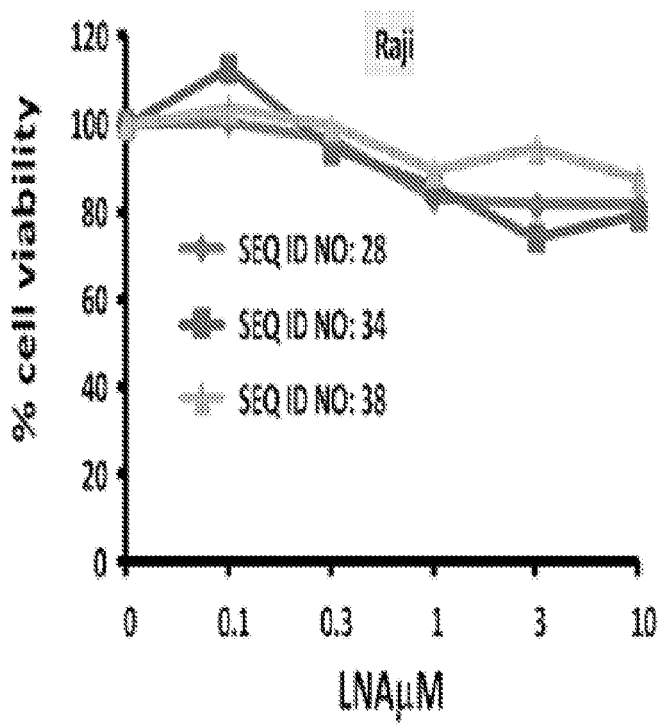
FIG. 6B is a graph representing the relative potency of LNA oligomers represented by SEQ ID NOs: 28, 34, and 38 with regard to their ability to inhibit proliferation of Raji human Burkitt's lymphoma cells. ATP levels were detected as an indicator of cell proliferation.
Figure 6C:
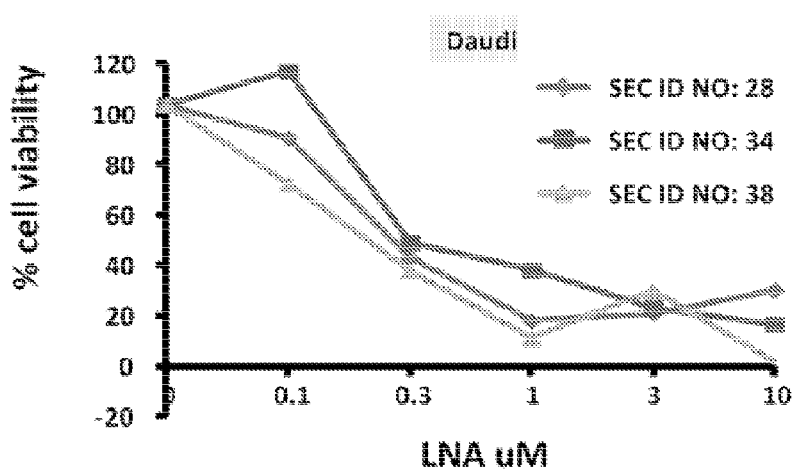
FIG. 6C is a graph representing the relative potency of LNA oligomers represented by SEQ ID NOs: 28, 34, and 38 with regard to their ability to inhibit proliferation of Daudi human Burkitt's lymphoma cells. ATP levels were detected as an indicator of cell proliferation.
Figure 6D:
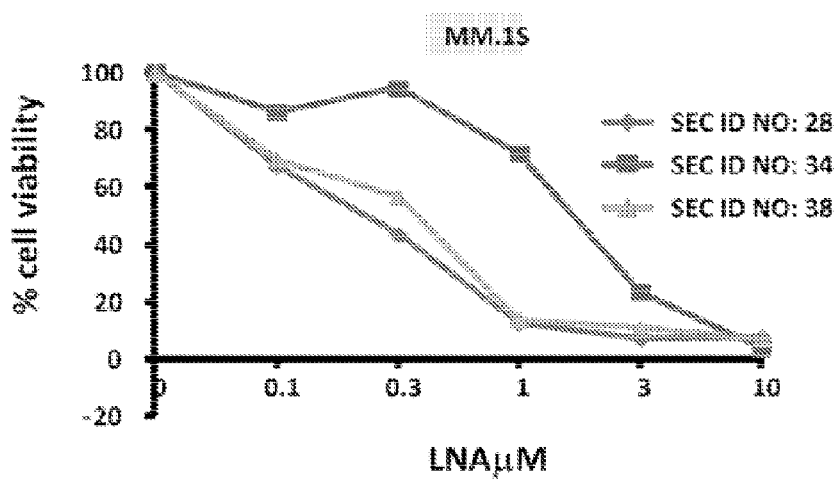
FIG. 6D is a graph representing the relative potency of LNA oligomers represented by SEQ ID NOs: 28, 34, and 38 with regard to their ability to inhibit proliferation of MM1.S human multiple myeloma cells. ATP levels were detected as an indicator of cell proliferation.

Time Course of Oligonucleotide Inhibition of Multiple Myeloma Cell Proliferation Antisense c-Myc oligonucleotides representing SEQ ID NOs: 28, 34, and 38 were evaluated for their ability to inhibit multiple myeloma cell proliferation over time. MM1.S human multiple myeloma cells were plated onto 24-well cell culture plates and treated with oligonucleotides representing SEQ ID NOs: 28, 34, and 38 at a final concentration of 10 µM. Cells were harvested at the varying time points as indicated in FIG. 5C. ATP levels were determined at each time point using the chemiluminescent reagent as in Example 10. ATP levels are shown in FIG. 5C as a percent of vehicle-treated cells (V). A non-specific oligonucleotide (NS) was used as a negative control. Error bars represent SEM (n=6).

12.12. Example 12

Potency of Oligomers on Inhibition of Multiple Myeloma Cell and Burkitt's Lymphoma Cell Proliferation Antisense oligonucleotides represented by SEQ ID NOs: 28, 34, and 38 were evaluated for their potency with regard to their ability to inhibit proliferation of three different Burkitt's lymphoma cell lines and a multiple myeloma cell line. The three Burkitt's lymphoma cell lines, Ramos, Raji, and Daudi as well as the multiple myeloma cell line MM1.S, were plated onto 96-well cell culture plates (40,000 cells/well). The cells were treated with the indicated concentration of each of the three oligomers. Cells were harvested after 5 days and ATP levels were measured as an indicator of cell proliferation as described in Example 10 (CellTiter-Glo®, Promega). See FIGS. 6A, 6B, 6C, and 6D.

What is claimed is:

1. An oligomer of between 10-30 nucleobases in length which comprises a contiguous nucleobase sequence of a total of between 10-16 nucleobases, wherein the contiguous nucleobase sequence comprises nucleotide analogues, and wherein the contiguous nucleobase sequence comprises between 0-2 mismatches to a corresponding region of a sequence selected from the group consisting of:

5'-TTCACCATGTCTCCTC-3'; (SEQ ID NO: 5)

5'-GGTACAAGCTGGAGGT-3'; (SEQ ID NO: 11)
and

5'-GTAGTTGTGCTGATGT-3', (SEQ ID NO: 15)
and, wherein the oligomer inhibits Myc expression in a cell or tissue.

2. The oligomer according to claim 1 wherein the nucleotide analogues comprise one or more sugar modified nucleotides.

3. The oligomer according to claim 2 wherein the one or more nucleotide analogues comprise LNA units.

4. The oligomer according to claim 2 wherein the nucleotide comprises a gapmer design.

5. The oligomer according to claim 4 selected from the group consisting of:

5'-$T_sT_s^{Me}C_sa_sc_sc_sa_st_sg_st_sc_st_sc_s^{Me}C_sT_s^{Me}C$-3'; (SEQ ID NO: 28)

5'-$G_sG_sT_sa_sc_sa_sa_sg_sc_st_sg_sg_sa_sG_sG_sT$-3'; (SEQ ID NO: 34)
and

5'-$G_sT_sA_sg_st_st_sg_st_sg_sc_st_sg_sa_sT_sG_sT$-3', (SEQ ID NO: 38)

wherein capital letters represent LNA monomers, lower case letters represent DNA monomers, subscript "s" represents a phosphorothioate linkage group between the monomers, and $^{Me}C$ denotes an LNA monomer containing a 5-methylcytosine base.

6. The oligomer according to claim 5 wherein the LNA units consist of beta-D-oxy-LNA monomers.

7. A conjugate comprising the oligomer according claim 1 covalently attached to at least one moiety that is not a nucleic acid or a monomer.

8. A pharmaceutical composition comprising the oligomer according to claim 1 and a pharmaceutically acceptable diluent, carrier, salt or adjuvant.

9. A method of inhibiting the expression of Myc in a cell, comprising contacting the cell with an effective amount of an oligomer according to claim 1.

10. The method of claim 9, wherein the cell is within a tissue of a mammal.

11. The method of claim 9, wherein the Myc is c-Myc.

12. The method of claim 9, wherein the Myc is N-Myc.

13. The method of claim 9, wherein the Myc is c-Myc and N-Myc.

14. A method of treating a cancer disease in a mammal, comprising administering to the mammal an effective amount of an oligomer according to claim 1, wherein the mammal is currently suffering from or at risk of suffering from the cancer disease.

15. The method of claim 14, wherein the mammal is a human.

16. The method of claim 14, wherein the cancer is selected from the group consisting of B-acute lymphocytic leukemia, Burkitt's lymphoma, diffuse large cell lymphoma, multiple myeloma, primary plasma cell leukemia, atypical carcinoid lung cancer, bladder cancer, breast cancer, cervical cancer, colon cancer, gastric cancer, glioblastoma, hepatocellular carcinoma, large cell neuroendocrine carcinoma, medulloblastoma, melanoma, neuroblastoma, oesophageal squamous cell carcinoma, osteosarcoma, ovarian cancer, prostate cancer, renal clear cell carcinoma retinoblastoma, rhabdomyocarcoma and small cell lung carcinoma.

17. The method of claim 16, wherein the cancer is selected from the group consisting of Burkitt's lymphoma, breast cancer, and multiple myeloma.

18. A pharmaceutical composition comprising a conjugate according to claim 7 and a pharmaceutically acceptable diluent, carrier, salt or adjuvant.

19. A method of inhibiting the expression of Myc in a cell, comprising contacting the cell with an effective amount of a conjugate according to claim 7.

20. A method of treating a cancer disease in a mammal, comprising administering to the mammal an effective amount of a conjugate according to claim 7, wherein the mammal is currently suffering from or at risk of suffering from the cancer disease.

* * * * *